(12) United States Patent
Espinosa et al.

(10) Patent No.: US 9,278,852 B2
(45) Date of Patent: *Mar. 8, 2016

(54) NANOTIPPED DEVICE AND METHOD

(75) Inventors: Horacio D. Espinosa, Winnetka, IL (US); Nicolaie A. Moldovan, Chicago, IL (US); Keun-Ho Kim, Evanston, IL (US)

(73) Assignee: Northwestern University, Evanston, IL (US)

( * ) Notice: Subject to any disclaimer, the term of this patent is extended or adjusted under 35 U.S.C. 154(b) by 1076 days.

This patent is subject to a terminal disclaimer.

(21) Appl. No.: 13/136,246

(22) Filed: Jul. 26, 2011

(65) Prior Publication Data

US 2012/0027947 A1 Feb. 2, 2012

Related U.S. Application Data

(62) Division of application No. 11/820,328, filed on Jun. 19, 2007, now Pat. No. 7,997,123, which is a division of application No. 10/801,928, filed on Mar. 16, 2004, now Pat. No. 7,250,139.

(60) Provisional application No. 60/455,898, filed on Mar. 19, 2003.

(51) Int. Cl.
*B01L 3/02* (2006.01)
*G01Q 60/54* (2010.01)
(Continued)

(52) U.S. Cl.
CPC .............. *B81C 1/00111* (2013.01); *B82Y 10/00* (2013.01); *G01Q 80/00* (2013.01); *Y10T 436/2575* (2015.01)

(58) Field of Classification Search
CPC .............................. B81C 1/00111; G01Q 80/00

USPC ..................... 73/105; 850/40, 56, 57, 60, 62
See application file for complete search history.

(56) References Cited

U.S. PATENT DOCUMENTS

| | | | |
|---|---|---|---|
| 4,410,290 A | 10/1983 | Ito et al. | 401/198 |
| 5,948,972 A | 9/1999 | Samsavar et al. | 73/105 |

(Continued)

OTHER PUBLICATIONS du Boer, M. et al., "Micromachining of Buried Channels in Silicon," J. Microelectromech, 9(1), Mar. 2000, pp. 94-103.

(Continued)

*Primary Examiner* — Daniel S Larkin

(57) ABSTRACT

A dispensing device has a cantilever comprising a plurality of thin films arranged relative to one another to define a microchannel in the cantilever and to define at least portions of a dispensing microtip proximate an end of the cantilever and communicated to the microchannel to receive material therefrom. The microchannel is communicated to a reservoir that supplies material to the microchannel. One or more reservoir-fed cantilevers may be formed on a semiconductor chip substrate. A sealing layer preferably is disposed on one of the first and second thin films and overlies outermost edges of the first and second thin films to seal the outermost edges against material leakage. Each cantilever includes an actuator, such as for example a piezoelectric actuator, to impart bending motion thereto. The microtip includes a pointed pyramidal or conical shaped microtip body and an annular shell spaced about the pointed microtip body to define a material-dispensing annulus thereabout. The working microtip may be used to dispense material onto a substrate, to probe a surface in scanning probe microscopy, to apply an electrical stimulus or record an electrical response on a surface in the presence of a local environment created around the tip by the material dispensed from the tip or to achieve other functions.

20 Claims, 32 Drawing Sheets

(51) Int. Cl.
  *B81C 1/00*  (2006.01)
  *B82Y 10/00*  (2011.01)
  *G01Q 80/00*  (2010.01)

(56) References Cited

U.S. PATENT DOCUMENTS

| 7,034,854 | B2 | 4/2006 | Cruchon-Dupeyrat et al. ............. 346/140.1 |
| 7,250,139 | B2* | 7/2007 | Espinosa et al. ............. 422/503 |
| 7,402,849 | B2* | 7/2008 | Liu et al. ............. 257/226 |
| 2004/0022681 | A1* | 2/2004 | Hantschel et al. ............. 422/63 |
| 2006/0057031 | A1 | 3/2006 | Hantschel et al. ............. 422/100 |

OTHER PUBLICATIONS

Hong, M. et al., "Scanning nanolithlography using a material-filled nanopipette," Appl. Phys. Lett., 77(16), Oct. 2000, pp. 2604-2606.

Hong, S. et al., "A Nanoplotter with Both Parallel and Serial Writing Capabilities," Science 288, Jun. 2000, pp. 1808-1811.

Lewis, A. et al., "Fountain pen nanochemistry: Atomic force control of chrome etching," Appl. Phys. Lett., 75(17), Oct. 1999, pp. 2689-2691.

Lieberman, K. et al., "Multifunctional, micropipette based force cantilevers for scanned probe microscopy," Appl. Phys. Lett. 65(5), Aug. 1994, pp. 648-650.

Minne, S. et al., Automated parallel high-speed atomic force microscopy, Appl. Phys/ Lett. 72(18), May 1998, pp. 2340-2342.

Minne, S. et al., Centimeter scale atomic force microscope imaging and lithography, Appi. Phys. Lett. 73(12), Sep. 1998, pp. 1742-1744.

Papautsky, I. et al., MicroMachined Pipette Arrays, IEEE Trans. Biomed. Eng. 47(6), pp. 812-819.

Piner, R. et al., Dip-Pen Nanolithography, Science 283, Jan. 1999, pp. 661-663.

Rangelow, I. et al, NANOJET: Tool for the nanofabrication, J.Vac. Sci. Technol. B 19(6), Nov./Dec. 2001, pp. 2723-2726.

Shalom, S. et al., A micropipette force probe suitable for near-field scanning optical microscopy, Rev. Sci. Instum. 63(9), Sep. 1992, pp. 4061-4065.

Vettiger, P. et al., The Millipede—More than one thousand tips for future AFM data storage, IBM J. Res. Devlop. 44(3), May 2000, pp. 323-340.

Vettiger, P. et al., The Millipede—Nanotechnology Entering Data Storage, IEEE Trans. On Nanotech. 1(1), Mar. 2002, pp. 39-55.

Zhang, M. et al., A MEMS nanoplotter with high-density parallel dip-pen nanolithography probe arrays, Nanotechnology 13, 2002, pp. 212-217.

Zou, J. et al., Conductivity-based contact sensing from probe arrays in dip-pen nanolithography, Appl. Phys. Letter. 83(3), Jul. 2003, pp. 581-583.

* cited by examiner

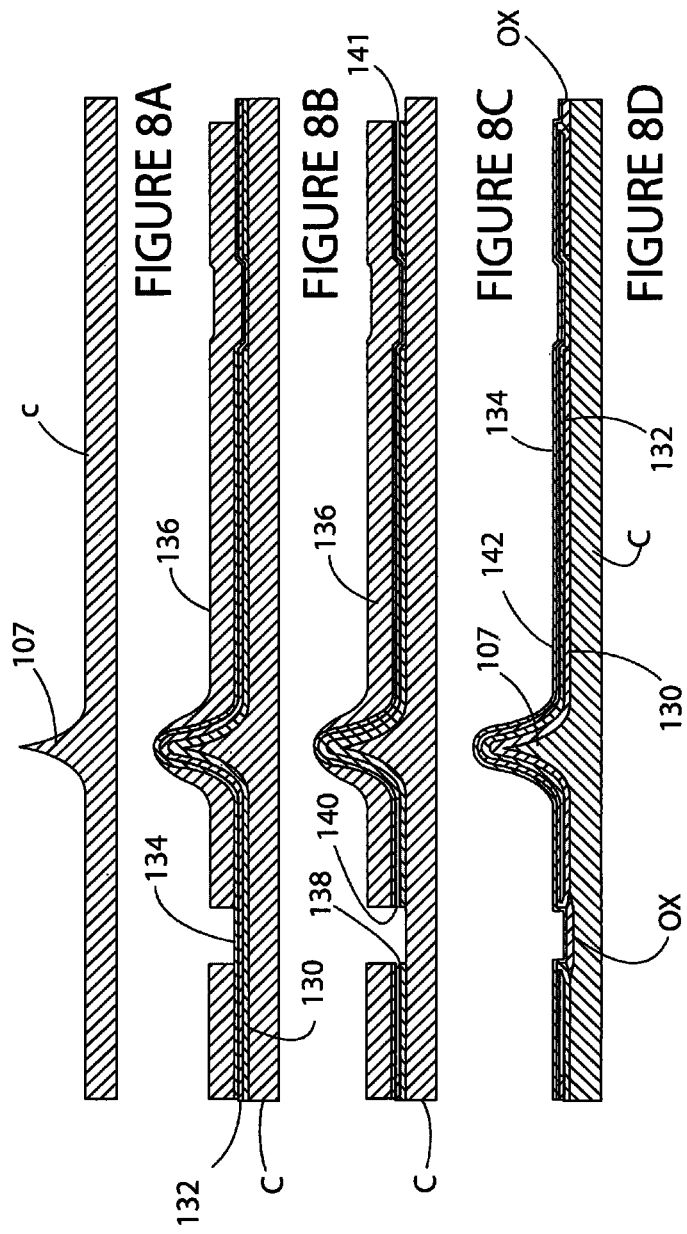

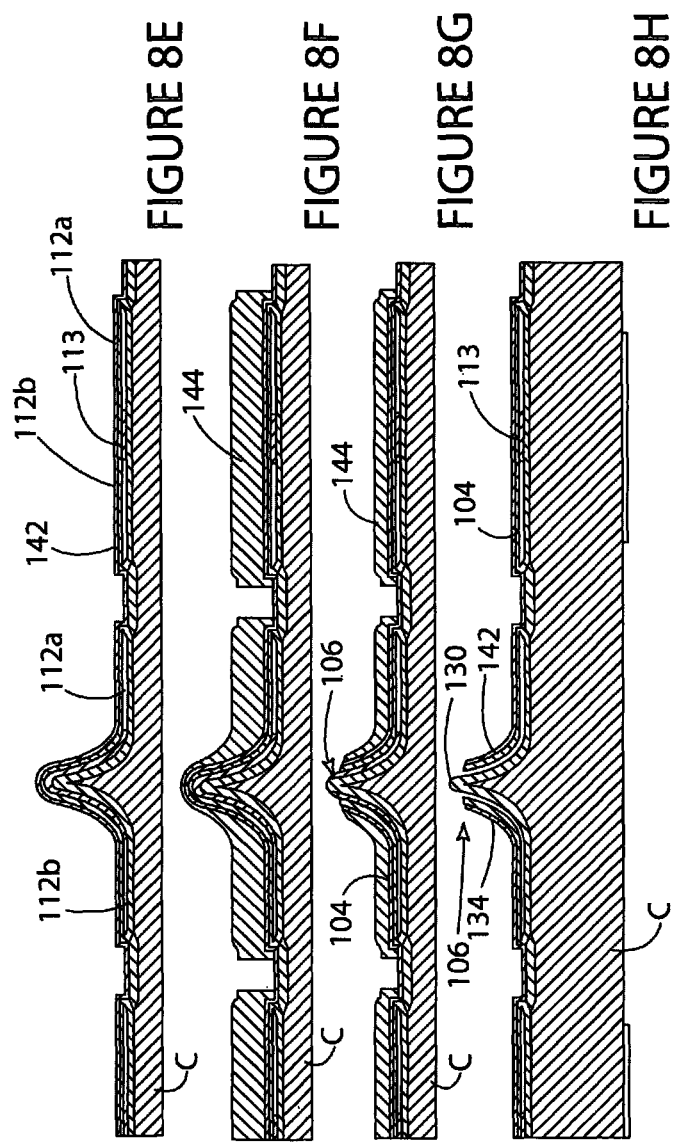

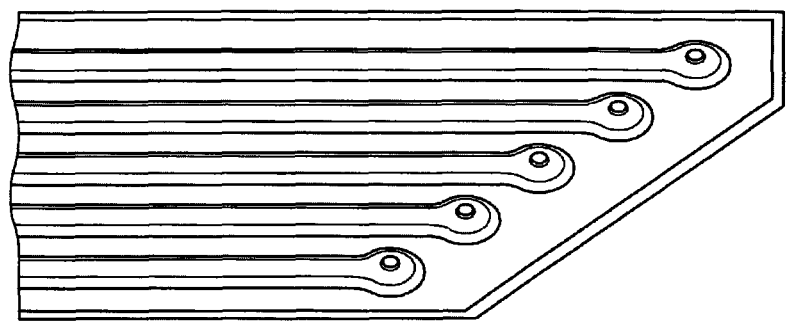
FIGURE 8J   40μm
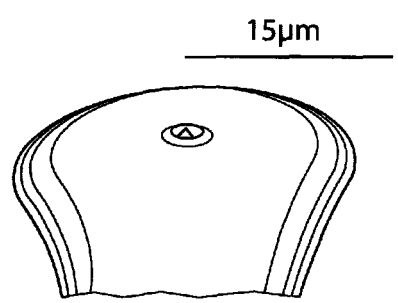
FIGURE 8K

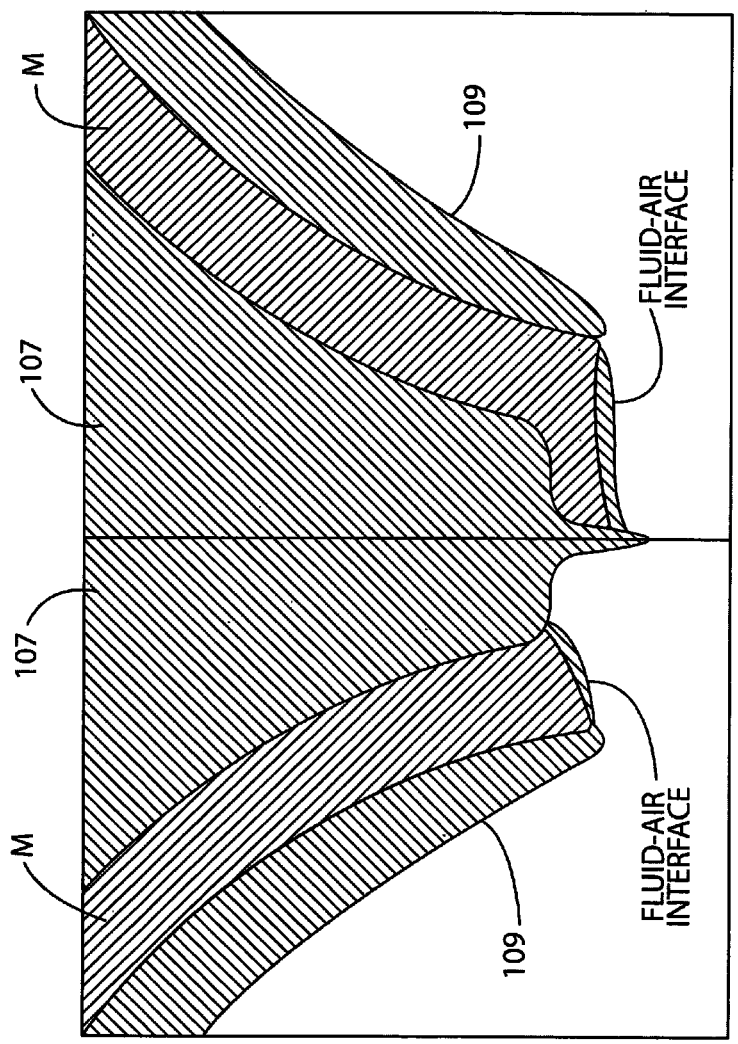

1μm

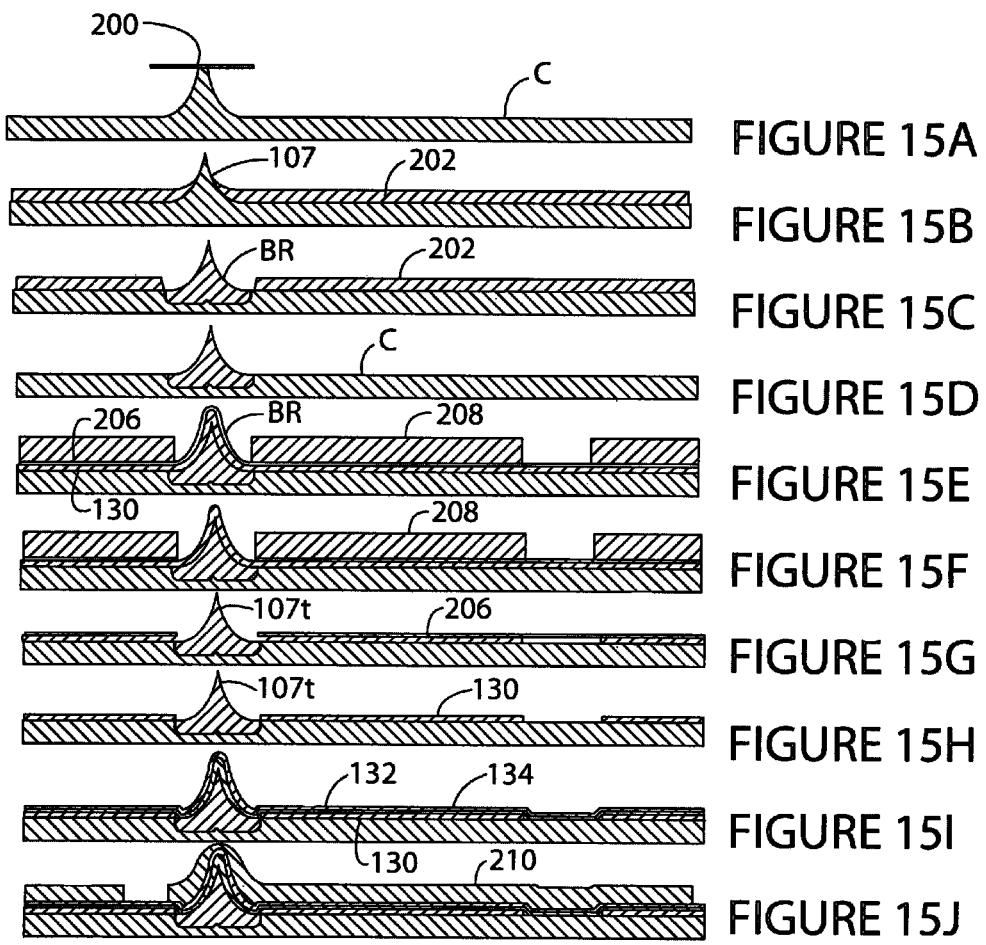

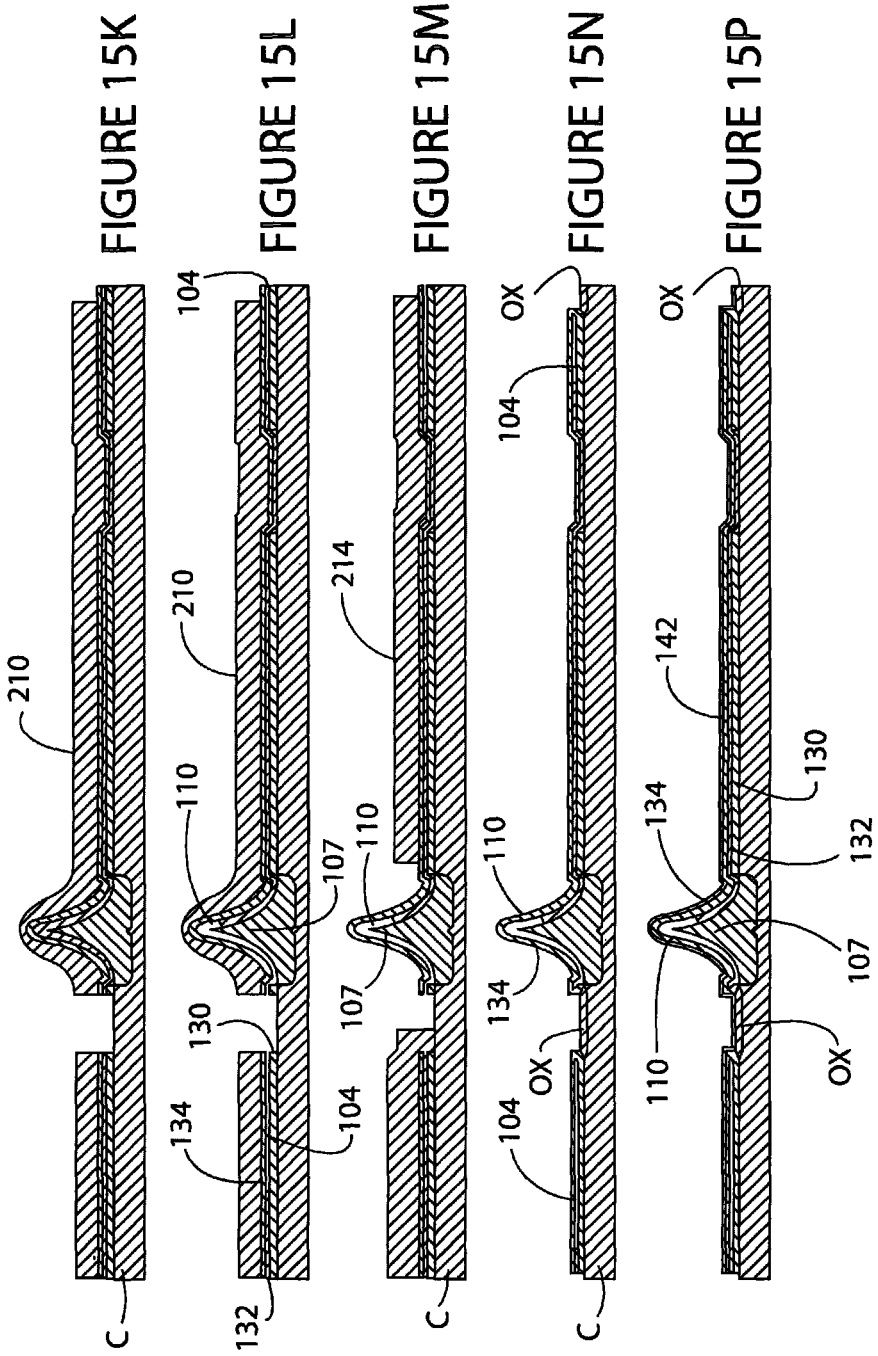

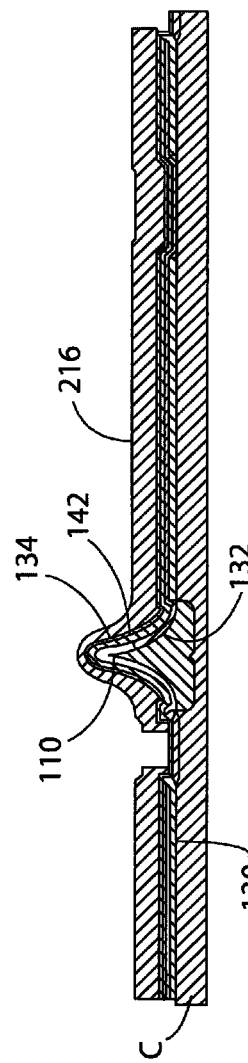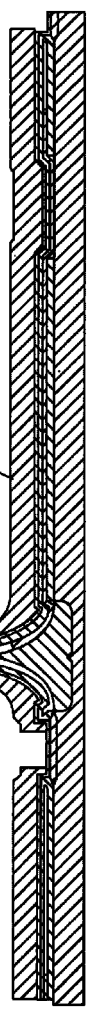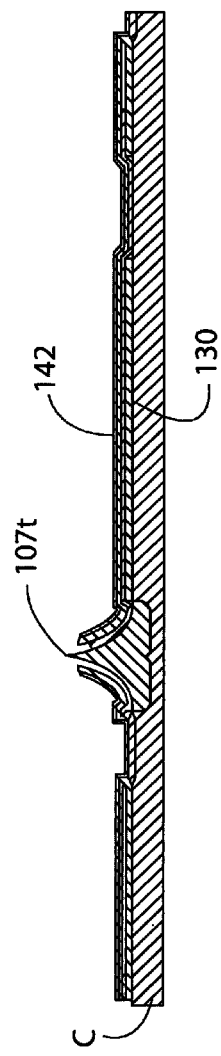

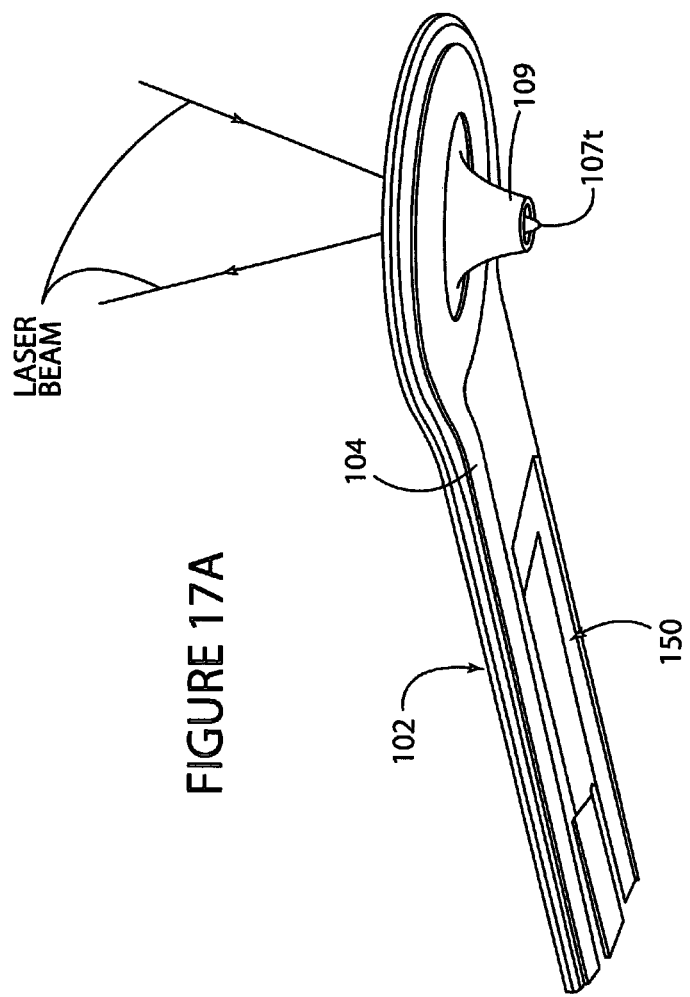

NANOTIPPED DEVICE AND METHOD

This application is a divisional of U.S. Ser. No. 11/820,328 filed Jun. 19, 2007, now U.S. Pat. No. 7,997,123, which is a divisional of U.S. Ser. No. 10/801,928, filed Mar. 16, 2004, now U.S. Pat. No. 7,250,139, which claims priority and benefits of provisional application No. 60/455,898 filed Mar. 19, 2003.

CONTRACTUAL ORIGIN OF THE INVENTION

This invention was made with government support under grant numbers EEC-0118025 and CMS-0120866 awarded by the National Science Foundation. The government has certain rights in the invention.

FIELD OF THE INVENTION

The present invention relates to a dispensing device having one or more cantilevers each with a dispensing microtip that is supplied with material via a microchannel in the cantilever and to microtips for other uses, as well as to methods of dispensing material using such devices and to methods of making such devices.

BACKGROUND OF THE INVENTION

Dip-pen nanolithography (DPN) has been developed to dispense material by molecular transport from a cantilever tip mounted on the probe of an atomic force microscope (AFM) onto a substrate surface as described in Science 283, 661 (1999). DPN is disadvantageous in that repeated re-inking of the dispensing tip is required to replenish molecules when large surface areas are to be patterned or when complex patterns are required. DPN also suffers from low speed and throughput due to its serial nature and limited scan size.

Another technique for nanopatterning involves a micropipette disposed on the tip of an AFM probe as described in Appl/Phys. Lett. 65 (5), 648 (1994). The micropipette technique suffers from the disadvantage of irregular shape of the micropipette, low reproducibility, and low resolution. The micropipette is difficult to integrate in array format to carry out massive pattering operations on one or more substrates.

Still another technique referred to as millipede:parallel read/write is described in IEEE Trans. on Nanotech. 1 (1), 39 (2002) and involves a cantilevered AFM probe having a heated tip able to write on a thermoplastic substrate by embossing the tip into the thermoplastic material. The technique does not dispense any material, but is illustrative for a massively parallel writing method using AFM probe arrays.

SUMMARY OF THE INVENTION

The present invention provides in an embodiment a dispensing device having a cantilever comprising a plurality of thin films arranged relative to one another to define a microchannel in the cantilever. A material dispensing microtip is disposed proximate an end of the cantilever and is communicated to the microchannel to receive material therefrom. In a particular embodiment, the microchannel is communicated to a reservoir that supplies material to the microchannel. One or more reservoir-fed cantilevers may be formed on a semiconductor chip substrate. A sealing layer preferably is disposed on one of a pair of thin films and overlies outermost edges of the thin films to seal any gap at the outermost edges against material leakage. The outermost edges of the pair of thin films may include angled regions extending from respective planar film regions and wherein the sealing layer resides between the thin films at the angled regions. The dispensing device may include an actuator, such as for example a piezoelectric actuator, on each cantilever to impart bending motion thereto.

In another embodiment of the invention, a device is provided having a working microtip with a pointed microtip body and an annular shell spaced about the pointed microtip body to define an annular space thereabout. The pointed tip body may be formed by the substrate or by a first thin film with the shell formed by another thin film. In a particular embodiment for dispensing material, the pointed microtip body comprises a material more hydrophilic than the material defining the shell. For example, a first thin film or the substrate of hydrophilic material can define the pointed microtip body and another thin film of less hydrophilic nature can define the shell. For purposes of illustration and not limitation, the working microtip may be used to dispense material onto a substrate, to probe a surface in scanning probe microscopy, to apply or record an electrical signal on a surface or to achieve other functions.

In still another embodiment of the invention, a method is provided for making a device of the types described above by forming on a substrate a plurality of thin films arranged relative to one another to define an elongated cantilever precursor having a microchannel extending at least partly along the length of the cantilever precursor, by forming a microtip proximate an end of the cantilever precursor and communicated to the microchannel, and by releasing a portion of the cantilever precursor from the substrate to form a cantilever extending from the substrate such that the cantilever has the microchannel and working microtip thereon. In a particular method embodiment, a material-containing reservoir is provided on a semiconductor chip substrate and one or more cantilevers extend(s) from the chip substrate.

In a further embodiment of the invention, a method is provided for making a microchannel by depositing first, second and third thin films on a substrate, removing an outermost edge region of the second thin film to form an open-sided microchannel between the first and third thin films, and sealing the outermost edge region of the open side of the microchannel by depositing a fourth thin film on one of the first and third thin films so as to overlie the outermost edge region of the open side.

In still a further embodiment of the invention, a method of making a working microtip involves forming a pointed tip on a substrate, depositing a plurality of thin films on the pointed tip, and removing regions of certain thin films about the pointed tip to form a material dispensing annular space about the pointed tip. In an additional embodiment of the invention, the fabrication of a sharper working microtip involves the formation of a pointed tip on a substrate, local ion implantation of the pointed tip with an etch stop, deposition of the first layer on the substrate, local removal of the first layer around the tip region to expose the ion implanted tip region, deposition of second and third thin films on the substrate, and removal of regions of the second and third thin films about the ion implanted pointed tip region to form an annular space disposed between the pointed tip and the third film and extending about the pointed tip.

In an even further embodiment of the invention, a method is provided to improve communication between the material dispensing annular space and the microchannel in the event the sealing layer is deposited by a CVD method on internal surfaces of the microchannel. The method involves, before applying the sealing layer, removing additional material from the second thin film concurrently and/or subsequently with removal of the outermost edges of the second thin film of the cantilever until the material dispensing annular space is formed about the pointed tip and communicates with the microchannel.

A method of nanopatterning pursuant to an embodiment of the invention involves supplying writing material through a microchannel in a cantilever extending from a substrate to a material dispensing microtip proximate an end of the cantilever and moving the dispensing microtip close enough to a surface to dispense the writing material thereon by diffusion-driven molecular transport from the microtip. A particular embodiment supplies writing material from a microreservoir on the substrate to the microchannel and then to the dispensing microtip by capillary action and/or diffusion. The writing material is dispensed through an annular space formed between a pointed microtip and an annular shell spaced about the microtip. The cantilever is moved during nanopatterning by imparting a bend to it, such as by energizing a thermal actuator or a piezoelectric film on the cantilever.

In practice of a further embodiment of the invention, a plurality of working microtips and cantilevers are integrated into linear or two dimensional arrays or stacks of two dimensional arrays to carry out parallel writing wherein each cantilever is controlled independently by, for example, addressing and actuating an actuator on each cantilever.

Further details and advantages of the present invention will become apparent from the following detailed description taken with the following drawings.

DESCRIPTION OF THE DRAWINGS

FIGS. 8A through 8I illustrate a microfabrication method according to an embodiment of the invention to make the cantilevers with microchannels and working microtips. FIGS. 8A through 8D and FIG. 8I relate to fabrication of features shown in FIG. 5 along line A-A'. FIGS. 8E-8I relate to fabrication of features shown in FIG. 6 along line B-B'. FIGS. 8J and 8K are photomicrographs of actual cantilevers and a microtip prior to release from the silicon chip substrate.

FIGS. 12A and 12B show two different configurations of the fluid-air interface achievable at the microtip of FIG. 11D.

FIGS. 15A through 15N, 15P through 15Q, 15S through 15V, and 15X through 15Y illustrate another method of fabrication of an embodiment of the invention to make the cantilevers with microchannels and ultrasharp material-dispensing microtips.

FIG. 17A is a schematic perspective view of the underside of a cantilever showing the integrated piezoelectric actuator and cantilever with microchannels and dispensing tip.

DESCRIPTION OF THE INVENTION

Figure 1:
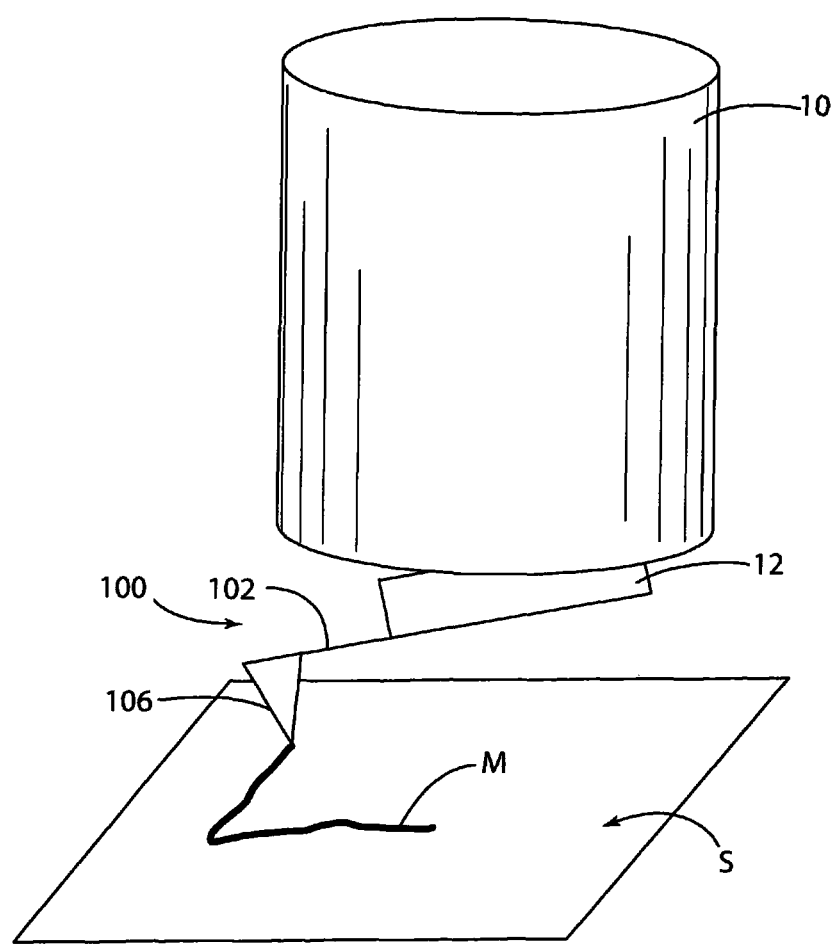
FIG. 1 is a schematic view of an atomic force microscope (AFM) head having a holder on which an illustrative writing material dispensing device shown schematically mounted thereon for writing on a surface.

Referring to FIG. 1, an atomic force microscope (AFM) scanning head 10 having a tip carrier 12 is illustrated schematically for purposes of illustration and not limitation. A dispensing device 100 pursuant to an illustrative embodiment of the invention is schematically shown disposed or mounted on the tip carrier 12 for movement (e.g. raster scanning) with the scanning head 10 to dispense writing material M on a surface S. More particularly, a silicon semiconductor chip having the dispensing device 100 fabricated thereon is mounted on the tip carrier 12 in the same manner as a conventional AFM probe tip such that the AFM hardware and software can be used to move the dispensing device to write a pattern with nanometer resolution of pattern features on surface S.

Figure 2:
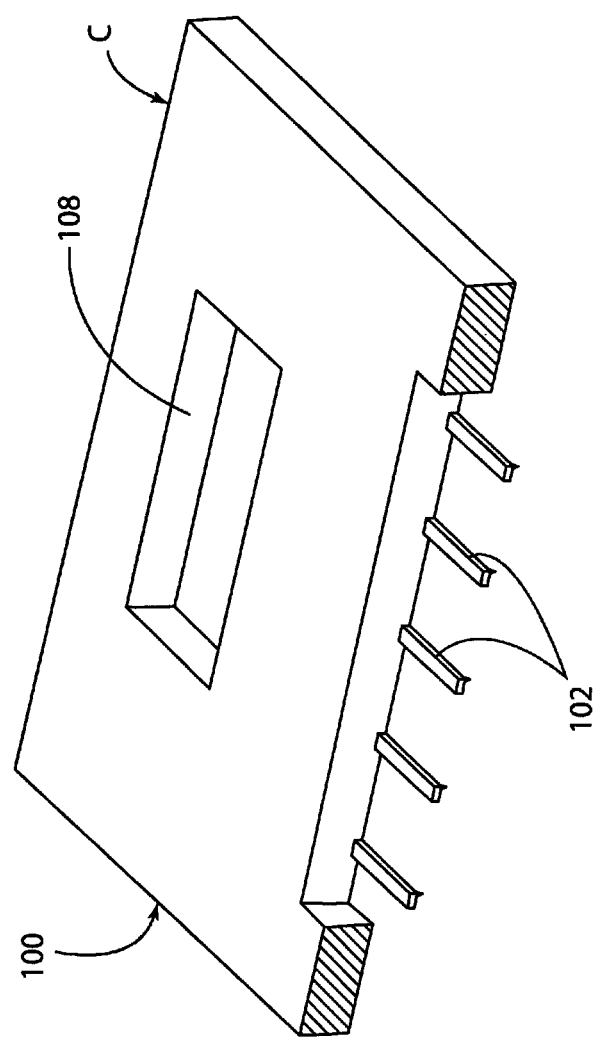
FIG. 2 is a schematic perspective view of a dispensing device pursuant to an illustrative embodiment of the invention.
Figure 3A:
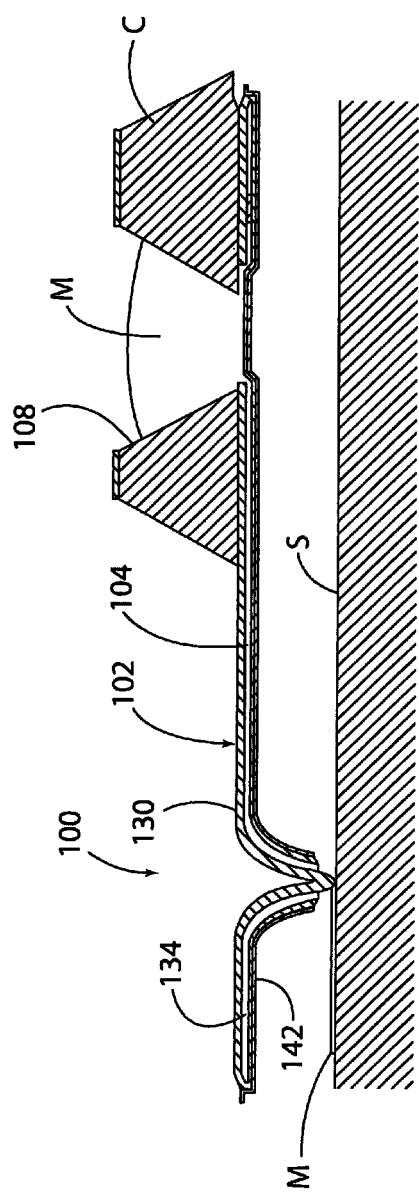
FIG. 3A is a longitudinal sectional view of a cantilever extending from a semiconductor chip substrate.
Figure 3B:
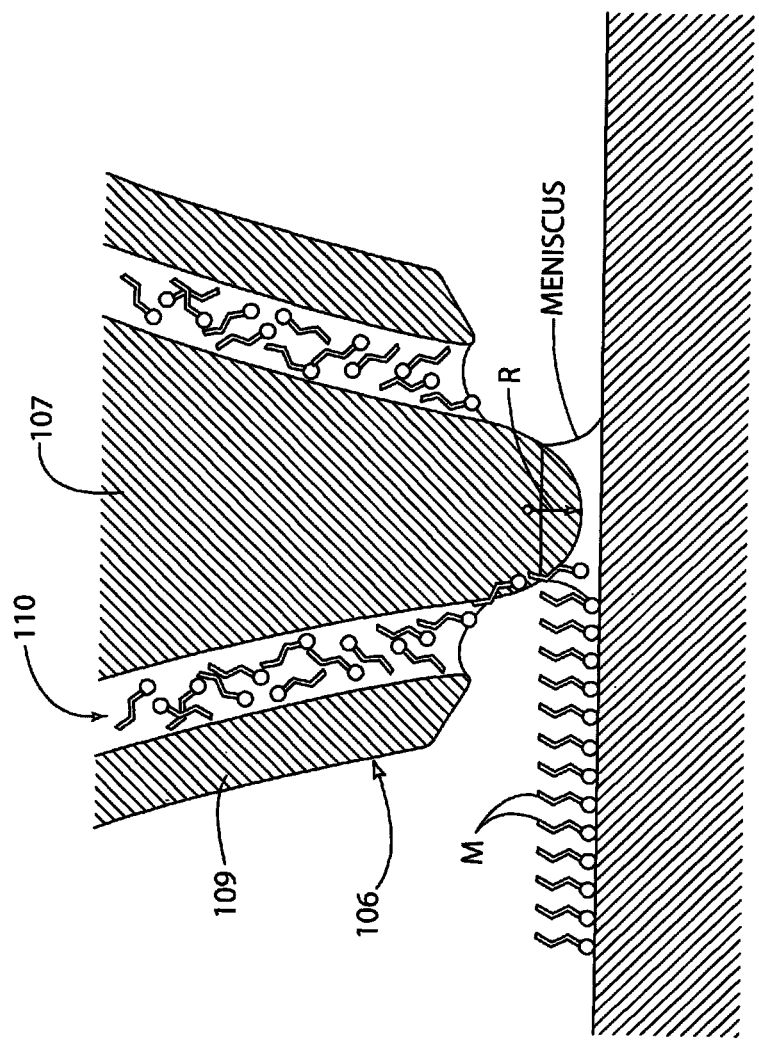
FIG. 3B is a partial sectional view of the dispensing microtip on the cantilever.
Figure 4A:
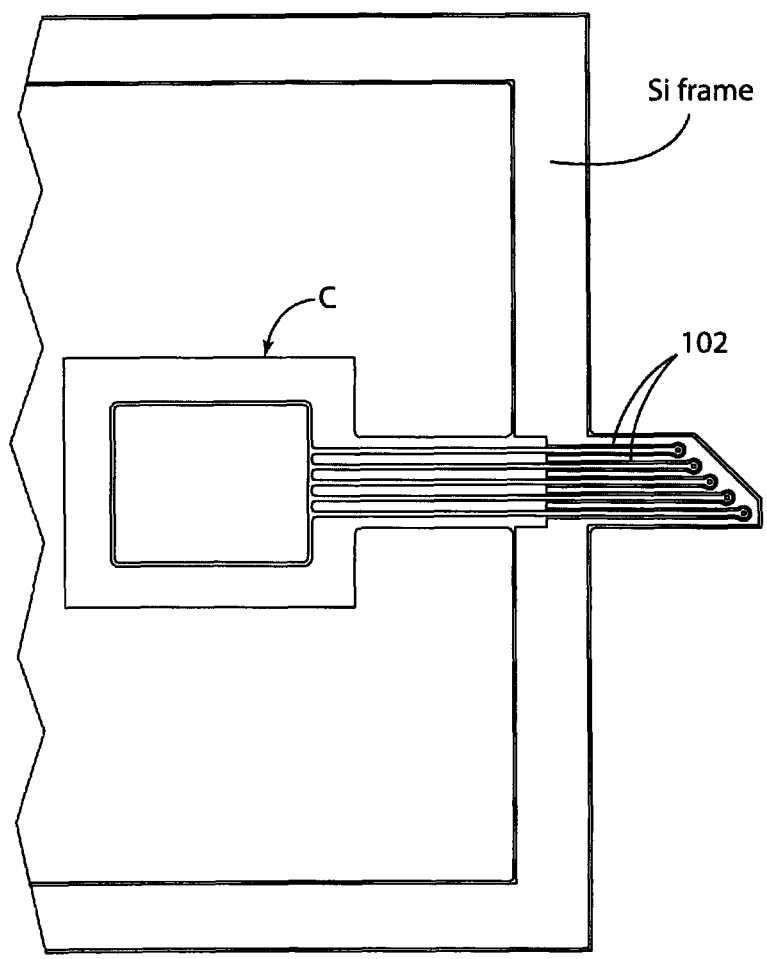
FIG. 4A shows a layout of an illustrative dispensing device for a semiconductor chip substrate.
Figure 4B:
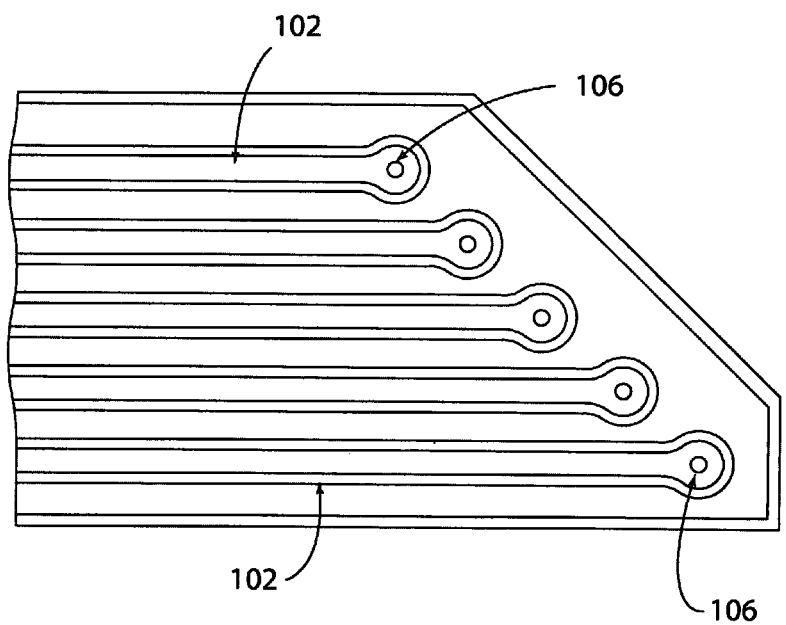
FIG. 4B shows the layout enlarged in the vicinity of the cantilevers.
Figure 5:
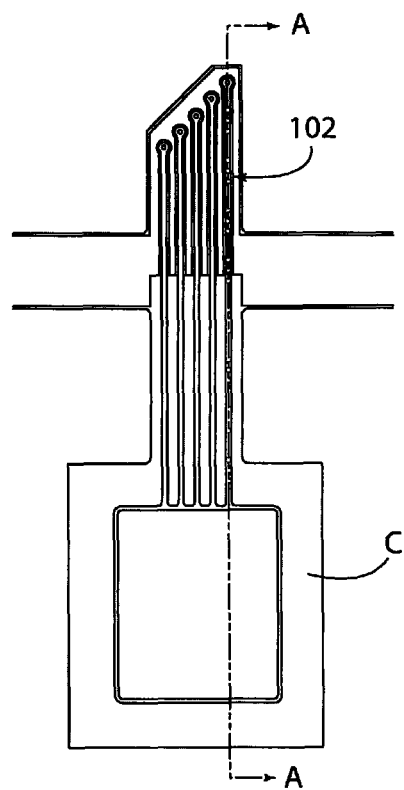
FIG. 5 is an enlarged view of the device layout of FIG. 4A.
Figure 6:
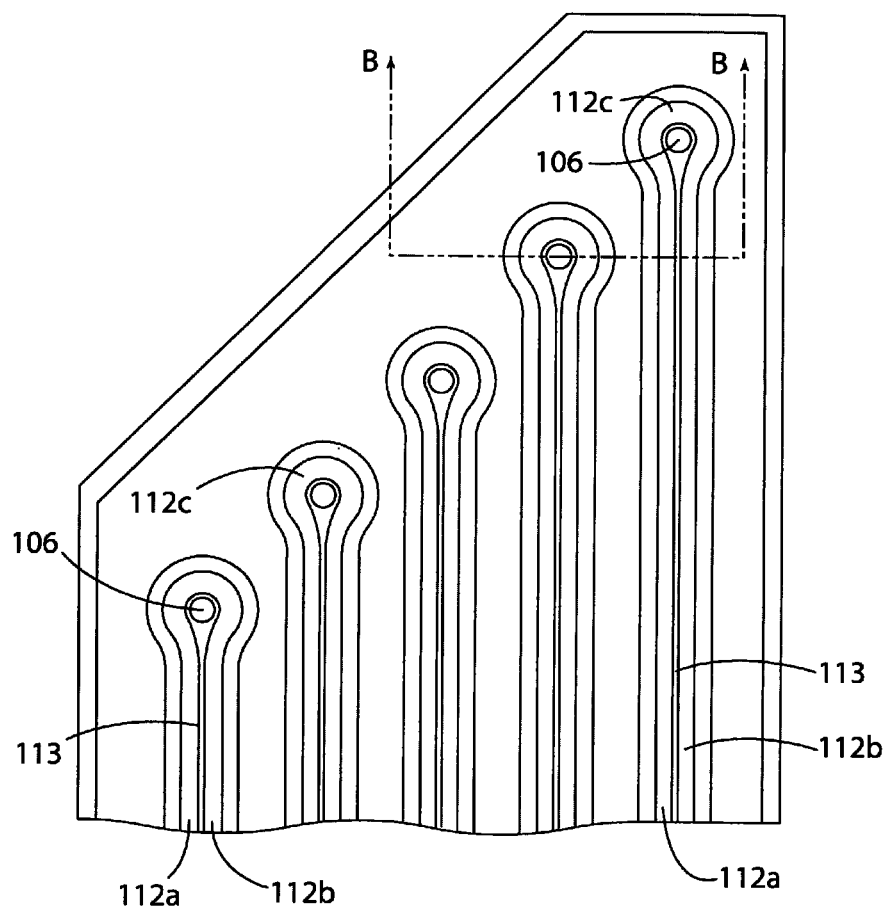
FIG. 6 is an enlarged view of the device layout of FIG. 4B.

Referring to FIGS. 2, 3A, and 3B, dispensing device 100 pursuant to an illustrative embodiment of the invention is shown schematically as comprising a semiconductor chip substrate C on which the dispensing device is fabricated by micromachining techniques as described below. The dispensing device 100 comprises one or more elongated cantilevers 102 that each comprise a plurality of thin films arranged relative to one another as described below to define an elongated cantilever body having a microchannel 104 therein and to define a material-dispensing working microtip 106 proximate an end of each cantilever remote from the chip substrate C. Each microtip 106 communicates with a respective microchannel 104 to receive material M therefrom to be dispensed from the microtip onto the surface S. In turn, each microchannel 104 communicates with a common material-containing reservoir 108 that supplies material M to the microchannel, although each microchannel may communicate with its own respective material-containing reservoir. In FIG. 3B, the fluid dispensing microtip 106 is shown comprising a pointed core tip body 107 having a radius R and an annular, generally truncated conical converging shell 109 spaced about the core tip to define a material dispensing annular space or annulus 110 residing about the core tip. The shell 109 converges in a direction toward the apex of the core tip body 107. To provide control of equilibrium of the fluid-air interface at the annulus 110, the core tip body 107 preferably comprises hydrophilic material (e.g. silicon nitride, silicon oxide, metals) and the shell 109 preferably comprises an equal or less hydrophilic material (e.g. silicon nitride, silicon, doped silicon).

Referring to FIGS. 4A, 4B, 5 and 6 which represent a device layout to be fabricated on the chip C for a particular exemplary embodiment of the invention, the microchannels 104 are shown having first and second side-by-side channel regions 112a, 112b (see FIG. 6) separated by a wall 113 with the channel regions 112a, 112b terminating in a common arcuate channel region 112c extending partially about the core tip body 107 to supply material thereto from the reservoir 108. In FIGS. 4A, 4B, 5 and 6, five cantilevers 102 of different lengths (e.g. from 300 microns to 500 microns with cantilever stiffness of 0.05 to 0.4 N/m) were formed extending from the chip C to evaluate cantilever length effects. The microchannels in the cantilevers 102 had a width of four to seven microns while the tip 107 had a height of three to five microns relative to the surface of the adjacent cantilever 102 for demonstration purposes.

In the embodiments of invention for dispensing material, the material M may comprise a writing fluid (designated as "ink") such as an alkanethiol liquid solution (e.g. saturated solution of 1-octadecanethiol in acetonitrile) onto surface S, which may comprise gold, for purposes of illustration and not limitation to form a nanopattern. The alkanethiol molecules are transported by diffusion and capillary action from the one or more microtips 106 to the gold surface and have a chemical affinity for the gold surface to attach thereto by chemisorption to form a monolayer. However, the invention is not limited to any particular writing fluid (liquid) or other material to be dispensed from microtips 106. For example, for purposes of illustration and not limitation, the material may comprise any chemical molecule, biomolecule (e.g. DNA, protein, etc.), or other species. The molecule or species may or may not be in a liquid aqueous or organic solution or dispersed in a liquid carrier. Moreover, a solid material may be dispensed from the dispensing device 100 by surface diffusion or a combination of surface diffusion and capillary action intermediated or facilitated by a meniscus formed by capillary condensation between the tip and the substrate of the moisture present in the ambient or adsorbed onto the substrate. For example, a writing material dispersed, dissolved or otherwise present in a fluid carrier is supplied from the reservoir through the microchannel to the microtip where the writing material may or may not solidify or transform to a solid or be present as a solid material sans the fluid carrier (e.g. the carrier fluid dries or is otherwise removed) at the microtip. Dispensing of the writing material from the microtip to the surface S can be facilitated by formation of a meniscus out of water present on the surface S and/or in the ambient environment or atmosphere. For purposes of illustration and not limitation, a material including, but not limited to, 1-octadecanethiol, may be dispensed from the microtips 106 by the combined diffusion/capillary condensation action mechanism.

The material, whether a fluid or a solid, can be deposited on surface S to form a pattern with nanometer resolution of pattern features, to initiate local reactions, to effect exchange of ions, to perform voltametry in nanometer-size confined spaces and for other purposes.

Potential applications for the dispensing device 100 include, but are not limited to, DNA nanopatterning involving depositing DNA for sequencing and/or synthesis, protheomics, combinatorial nanochemistry, nanolithography involving dispensing photoresist or other resist materials, scanning probe microelectrochemistry involving imaging, etching, deposition, and nanovoltametry, scanning probe chemistry involving etching, deposition, and mask repair, and nanojets and atom guns involving localized delivery of free radicals and atom species.

Furthermore, in practice of the invention, the cantilevers 102 with microtips 106 are not limited to applications where a material is dispensed from the microtips. For example, a working microtip 106 may be used to probe a surface in scanning probe microscopy, to apply or record an electrical signal on a surface, or to achieve other functions without dispensing any material therefrom.

The microfabrication process of the dispensing device 100 uses the device layouts shown in FIGS. 4A, 4B, 5 and 6 and begins with a {100} single crystal silicon chip substrate.

Figure 7A:
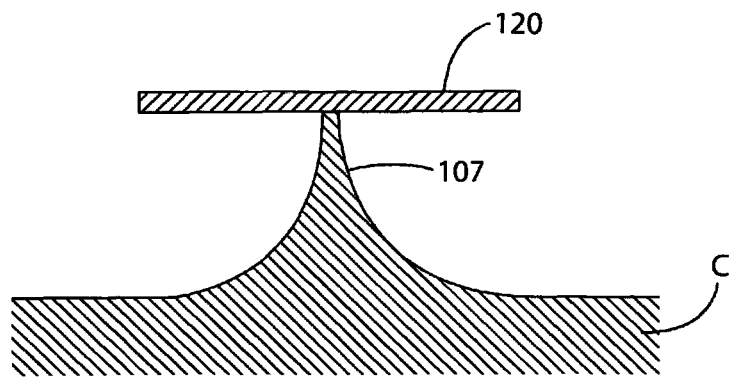
FIGS. 7A, 7B, 7C illustrate a method of fabrication of the working microtip.
Figure 7B:
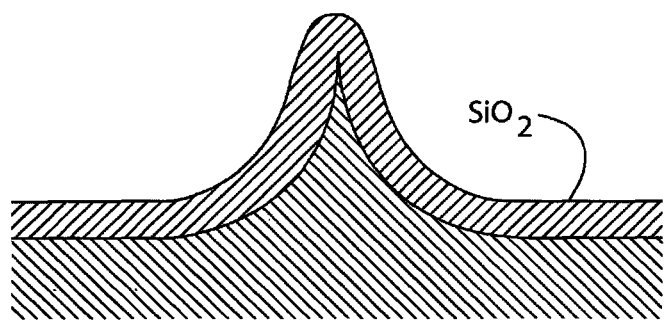
Figure 7C:
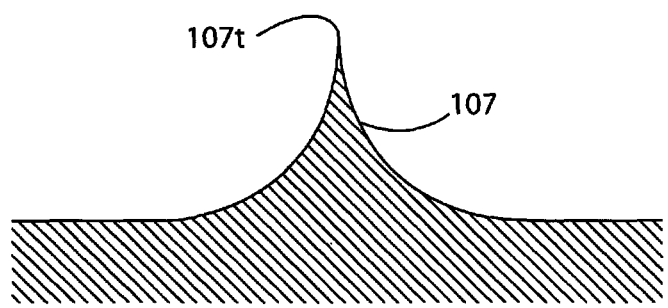
Figure 7D:
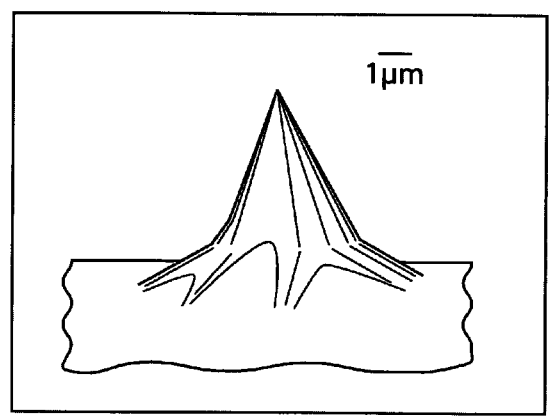
FIG. 7D is a photomicrograph of a microtip made by the method of fabrication.

Referring to FIGS. 7A, 7B, 7C, each core tip body 107 is first formed on the chip substrate C. For example, for each core tip body 107, a mask 120 is placed on the chip substrate C, and the chip is etched using one or more of various conventional etchants to form the pyramidal-shaped (or other shape) core tip body 107. A suitable etching treatment comprises a KOH etching in 40% (mass ratio) KOH and HNA etching in hydrofluoric-nitric-acetic acid mixture (3:5:3 by volume), although other etchants can be used including, but not limited to, $XeF_2$, $SF_6$ reactive ion etching, and the like. The pointed tip body 107 is sharpened by oxidizing the etched chip substrate C to thermally grow a $SiO_2$ layer thereon, FIG. 7B, followed by wet etching of the oxidized chip substrate using buffered hydrofluoric acid process. The core tip bodies 107 are formed concurrently on the chip substrate C in this way. A plurality of individual pointed, pyramidal-shaped or conical-shaped tip bodies 107 having tips 107t thereby are formed on the chip substrate, FIGS. 7C and 7D.

FIGS. 8A through 8I illustrate a microfabrication method for forming a cantilever 102 on the chip substrate C (having the core tip bodies 107) pursuant to a method embodiment of the invention. Each cantilever 102 is communicated to reservoir 108 via microchannel 104, FIGS. 8A through 8I. All of the cantilevers 102 are formed concurrently on the chip substrate using the method illustrated wherein FIGS. 8A through 8D and 8I relate to fabrication of features shown in FIG. 5 along lines A-A' and FIGS. 8E-8H relate to fabrication of features shown in FIG. 6 along lines B-B'.

Referring to FIG. 8A, the chip substrate is shown with a core tip body 107 formed as described above. In FIG. 8B, a first thin film or layer 130 of $Si_3N_4$ (e.g. 0.25 microns thick) is deposited by LPCVD (low pressure chemical vapor deposition) on the chip substrate. Then, a second thin film or layer 132 of $SiO_2$ (e.g. 0.5 microns thick) is deposited by LPCVD on the first thin film 130. Then, a third thin film or layer 134 of $Si_3N_4$ (e.g. 0.3 microns thick) is deposited by LPCVD on the second thin film 132. A photoresist layer 136 then is applied on thin film 134, FIG. 8B.

Referring to FIG. 8C, the thin film coated chip C is patterned with photoresist layer 136 and then etched using $CF_4$ reactive ion etching (RIE) for etching the third layer (nitride) and using buffered hydrofluoric acid solution to selectively remove a portion of the $SiO_2$ film or layer 132 as shown to produce the undercuts 138, 140, 141 which will form portions of the microchannel in the cantilever. FIG. 8D taken along line A-A' and 8E taken along line B-B' show enclosure of the open edges of the undercuts 138, 140, 141 by selective oxidation of the silicon chip substrate by thermal wet oxidation process to produce a "bird's beak".

Figure 8I:
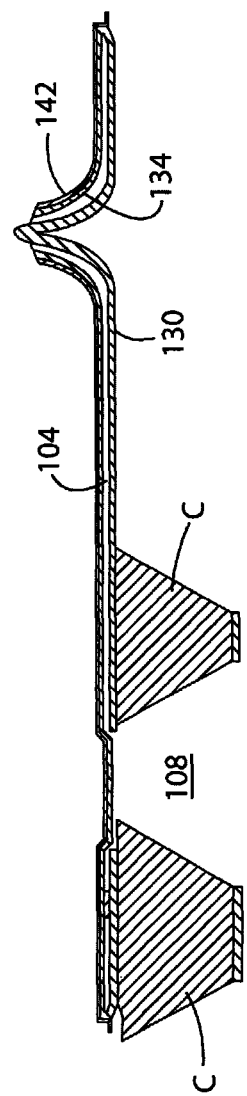
Figure 9A:
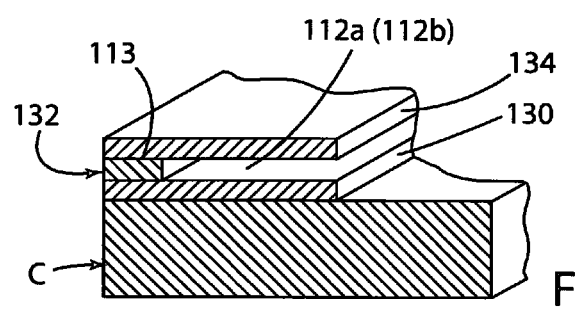
FIGS. 9A, 9B, 9C illustrate a method of fabrication of the microchannels.

FIG. 9A illustrates partial etching of the $SiO_2$ layer 132 that occurs to form open sided microchannel regions 112a, 112b separated by and on opposite sides of wall 113 on each cantilever 102 concurrently with formation of the undercuts 138, 140, 141 of FIG. 8C.

Figure 9B:
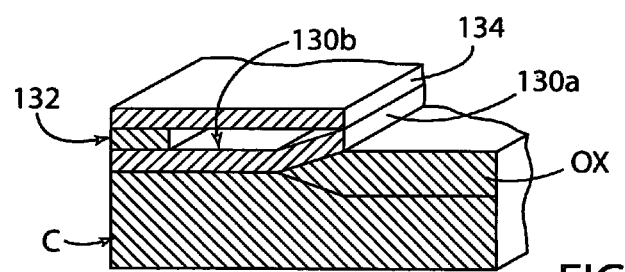

FIG. 9B shows the effect of selective oxidation of the chip substrate C at areas OX to cause the first film or layer 130 to bend toward the third film or layer 134 to form an outermost angled region 130a at an outmost edge thereof concurrently with the selective oxidation of FIG. 8D. The angled region 130a extends from a generally planar region 130b of the first film or layer 130.

Figure 9C:
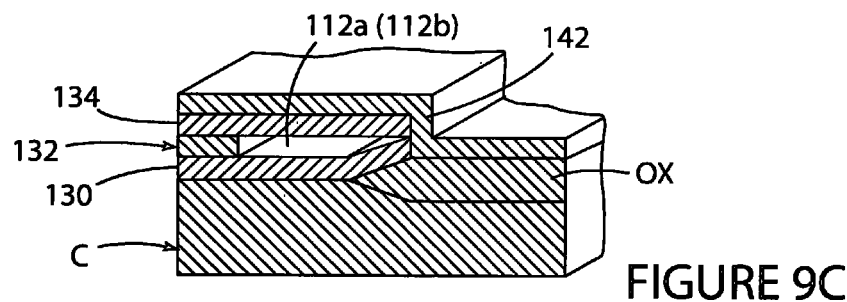
Figure 10:
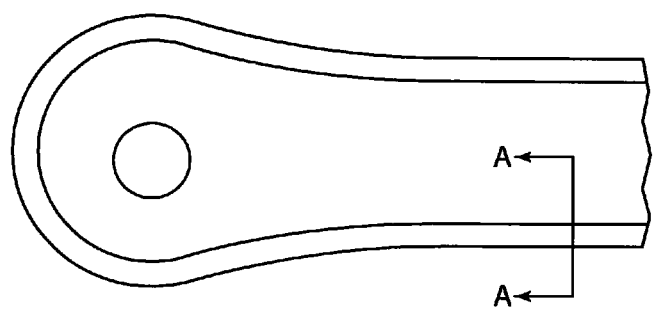
FIG. 10 is a photomicrograph of an end portion of a cantilever made by the microfabrication method.

Then, the selective oxidation step is followed by deposition of a sealing layer 142 by sputtering, or evaporation or CVD process as illustrated in FIG. 8D along lines B-B' and in FIG. 9C. The sealing layer 142 can comprise $Si_3N_4$ or polycrystalline silicon (Poly-Si) sealing material, or any other suitable sealing material. The sealing layer 142 overlies the outermost edges of the first and third films as shown best in FIG. 9C to prevent leakage of fluid or material from the microchannel regions 112a, 112b. FIG. 10 is a photomicrograph of a cantilever 102 after the sealing layer 142 is deposited thereon as illustrated in FIGS. 9A through 9C, which are taken along lines A-A' of FIG. 10.

Referring to FIG. 8F through FIG. 8I, photoresist 144 is deposited in the desired pattern on the sealing layer 142, FIG. 8F. The photoresist 144 is partially removed by oxygen RIE (reactive ion etching) to expose the apex or end of the microtip 106, FIG. 8G.

Then, the exposed apex of the microtip, starting with the sealing layer and continued with the third layer, is etched by $CF_4$ RIE, FIG. 8G. The remaining photoresist is removed by oxygen plasma. The selective removal by buffered hydrofluoric solution of the second thin film or layer 132 of $SiO_2$ from between the first and third films or layers 130, 134 at the core tip body 107, FIG. 8H, occurs until the annular space or annulus 110 so formed communicates with the microchannel. This completes the formation of the volcano-shaped microtip 106, FIG. 8I which is taken along lines A-A' of FIG. 5. The microtip 106 thereby is formed to include pointed core tip body 107 and an annular, generally conical converging shell 109 (comprised of the third film or layer 134) spaced about the core tip body to define a material dispensing annular space or annulus 110 residing about the core tip body. The sealing layer 142 resides on the conical converging shell 109. FIGS. 8J and 8K are photomicrographs of cantilevers and a microtip prior to release from the chip substrate.

Figure 8L:
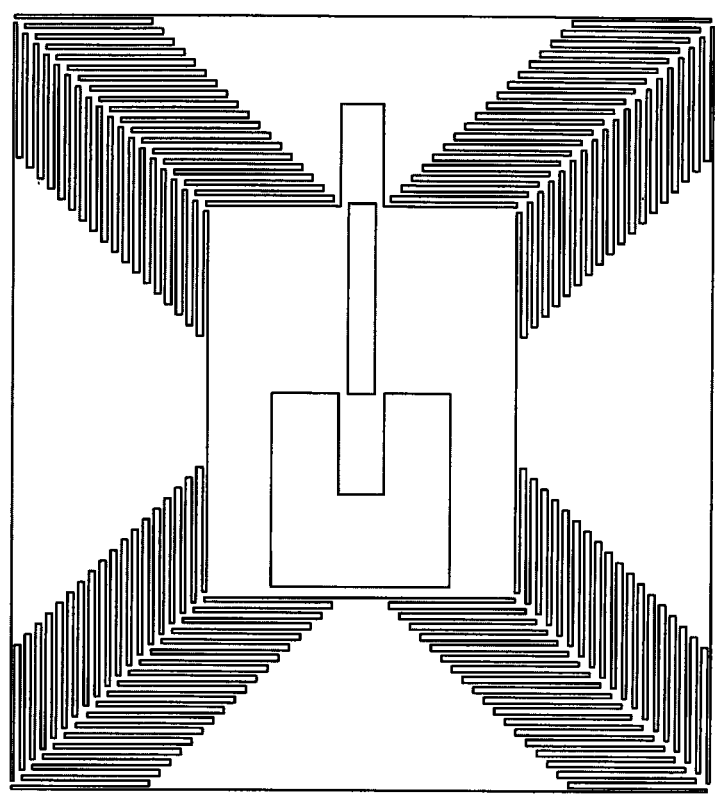
FIG. 8L shows a backside release mask.

Then, a KOH or other etching step is conducted to release the cantilevers 102 from the Si substrate. In this final etching step, the reservoir 108 also is formed in the chip substrate so as to be in fluid flow communication with the microchannels 104 on the cantilevers 102. The dispensing device 100 eventually is released from the silicon substrate by the KOH etching from the backside of the chip substrate with a suitable backside release mask designated shown in FIG. 8L present on the backside. The backside release mask eventually contains convex corner compensation beams such as described in Sensors and Actuators, Vol. 3, p.127, 1992, incorporated herein by reference. KOH etching involves wet etching of the chip substrate using 40% (mass ratio) KOH at 80 degrees C. Subsequently, the side of the chip opposing the tip will be coated by evaporation with a reflective metal film, such as Au (gold) 15 nm, to provide better reflection of the laser beam eventually used for the AFM head positioning control (optical lever). The dispensing device 100 of FIG. 3A is thereby microfabricated on the silicon substrate chip.

For purposes of illustration and not limitation, the microfabrication method described above can be used to produce individual cantilevers 102 having a length of about 100 microns to about 500 microns and including a microchannel 102 having a width dimension in the range of about four to about ten microns and a height dimension in the range of about 0.05 to about 1.5 microns. Flow rate of fluid through a microchannel is affected by channel dimensions, fluid wetting properties of the microtip and materials of the microtip and microchannel, the chemical pretreatment, and fluid viscosity. Similarly, the core tip body 107 can be produced to have an apex having a height of about three to about five microns of the tip relative to a plane of the cantilever (0.5 to 1.5 microns above the plane defined by the end of the shell 109). The inner radius of the end of the shell 109 measured from the apex of the core tip body 107 can be in the range of 0.5 to 2 microns.

Figure 11A:
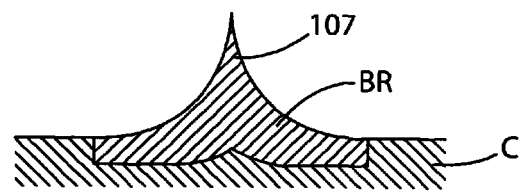
FIGS. 11A, 11B, 11C, 11D, 11E illustrate another method of fabrication of the microtip.
Figure 11B:
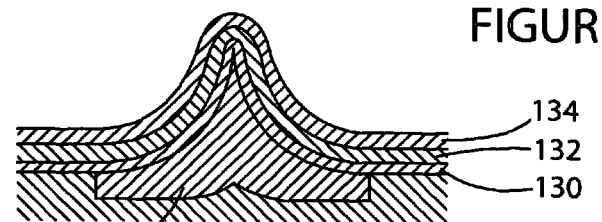
Figure 11C:
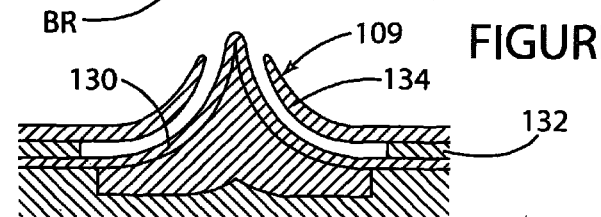
Figure 11D:
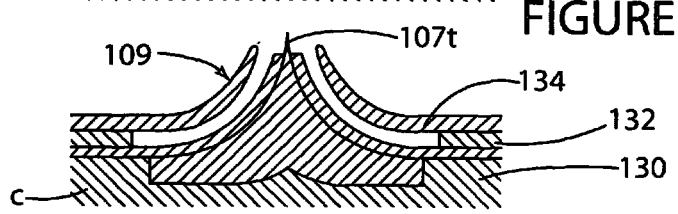
Figure 11E:
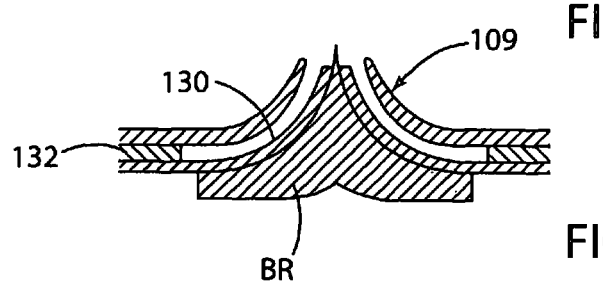

FIGS. 11A through 11D illustrate an alternative embodiment for forming the microtip wherein like reference numerals are used to designate like features of previous figures. In FIG. 11A, the core top body 107 is illustrated as having been doped with boron (B) which doped region BR functions as an etch stop during later KOH etching step for the release of the cantilever illustrated in FIG. 11E, to form the volcano-shaped microtip 106 differing from that of FIGS. 3A and 8I in having a pointed end 107t of the boron doped core tip body 107 protruding above the first thin film or layer 130 of $Si_3N_4$ as shown in Figs. 11D and 11E. Such a microtip of FIGS. 11D-11E permits two possible configurations for the fluid-air interface at the microtip 106 as illustrated in FIGS. 12A, 12B, respectively. A pressure pulse of about one atmosphere on the fluid is needed to switch from the fluid-air interface of FIG. 12A to that of FIG. 12B. An alternative way to bring the fluid interface to that of FIG. 12B is to dip the dispensing tip into liquid.

Figure 13A:
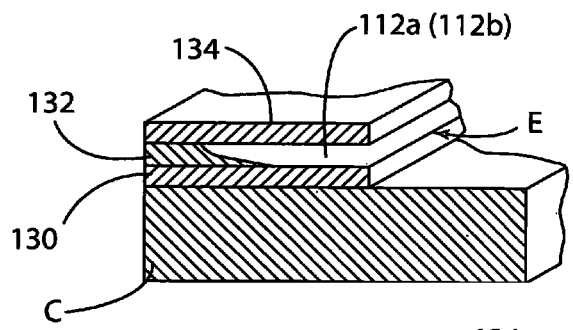
FIGS. 13A, 13B, 13C, 13D illustrate sealing of the longitudinal edge or side of a microchannel wherein the sealing layer is deposited in the microchannel.
Figure 13B:
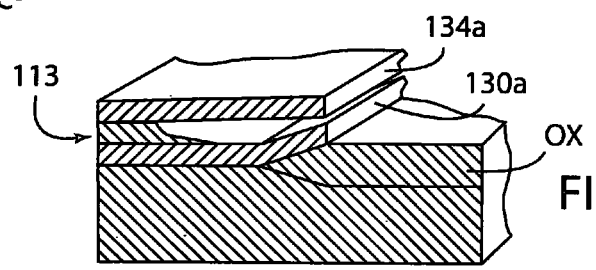
Figure 13C:
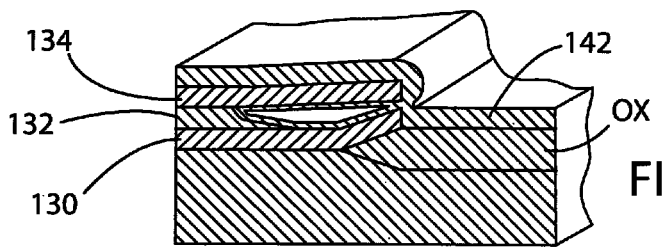
Figure 13D:
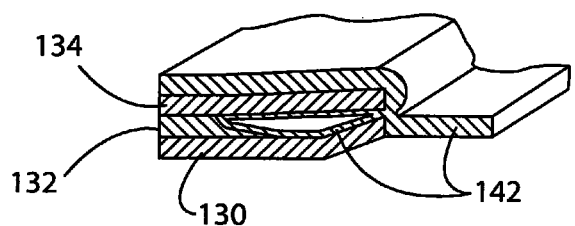
Figure 13E:
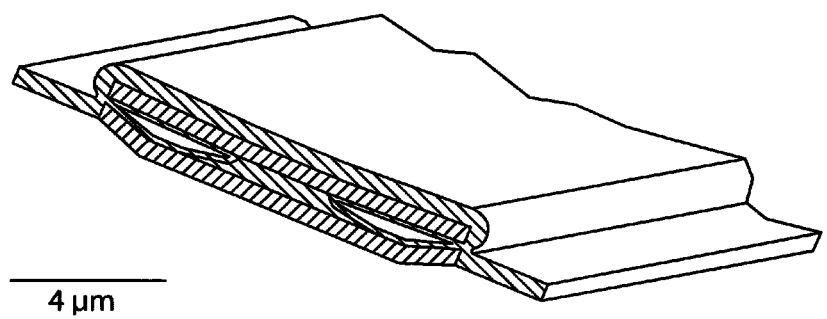
FIG. 13 E is a photomicrograph of a transversely sectioned cantilever sealed by a sealing layer that extends inside the microchannel pursuant to FIG. 13D.
FIG. 13F is a photomicrograph of the dispensing end of a cantilever sealed by a sealing layer.
FIG. 13G is a photomicrograph of the microtip along the dotted lines of FIG. 13F.
Figure 13F:
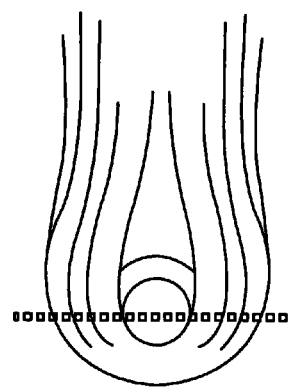
Figure 13G:
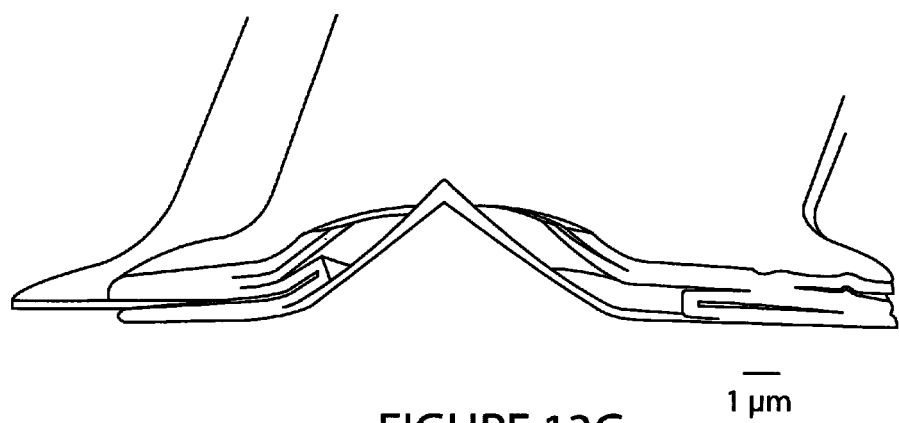

FIGS. 13A, 13B, 13C illustrate an alternative embodiment for sealing of the longitudinal edge or side E of a microchannel regions 112a, 112b defined between the first and third thin films or layers 130, 134 of $Si_3N_4$ and separated by wall 113 formed by partially etching the second thin film or layer 132 of $SiO_2$. In this alternative embodiment, the sealing layer 142 is deposited in the microchannel regions 112a, 112b. For example, referring to FIG. 13B, during the selective oxidation step where the chip substrate C is oxidized at areas OX ($SiO_2$), both the first and third thin films or layers 130, 134 have been observed to bend slightly away from the chip substrate so as to have angled regions 130a, 134a at outermost edges thereof. A small gap is formed between the angled regions 130a, 134a, as illustrated in FIG. 13B. Subsequent deposition of the sealing layer 142 by LPCVD has been found to result in deposition of the sealing layer 142 on the surfaces inside the microchannel regions 112a, 112b as illustrated in FIG. 13C (before etching of the substrate chip) and FIG. 13D (after etching of the chip substrate) to effect sealing of the microchannel regions. The internal deposition of the sealing layer on the inner walls of the microchannels does not reduce substantially the cross section and the fluid transport in the channels, since there is a fluid transport (flow) only during the filling of the microchannel, not during the writing process, which relies mostly on the diffusion of ink molecular species along the channels, rather than a flow of the fluid ink itself. However, the deposition of the sealing layer on the inner sidewall of the microchannels may hinder the establishing of the connectivity between the microchannel and the shell-to-core gap 110 of the dispensing tip, during the etching step illustrated in FIG. 8I. FIG. 13E is a photomicrograph showing the sealing layer deposited inside the microchannel regions of an actual microfabricated cantilever that has been transversely sectioned by a focused ion beam. FIG. 13F is a photomicrograph showing the sealed microchannel regions of an actual microfabricated microtip that has been transversely sectioned through the microtip. FIG. 13G is a photomicrograph showing the sealing layer deposited inside the microchannel regions around the core tip of an actual microfabricated microtip that has been transversely sectioned by focused ion beam along the dotted line of FIG. 13F. Thus, the fabrication method described by FIGS. 8A-8I typically are used only for sealing layers deposited by low conformity processes, such as evaporation and sputtering.

Figure 14A:
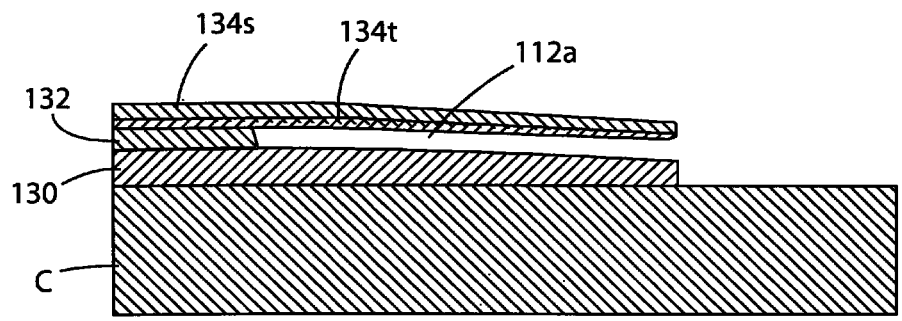
FIGS. 14A, 14B, 14C illustrate another alternative embodiment for sealing of the longitudinal edge or side of a microchannel wherein deposition of the sealing layer on surfaces in the microchannel is reduced.
Figure 14B:
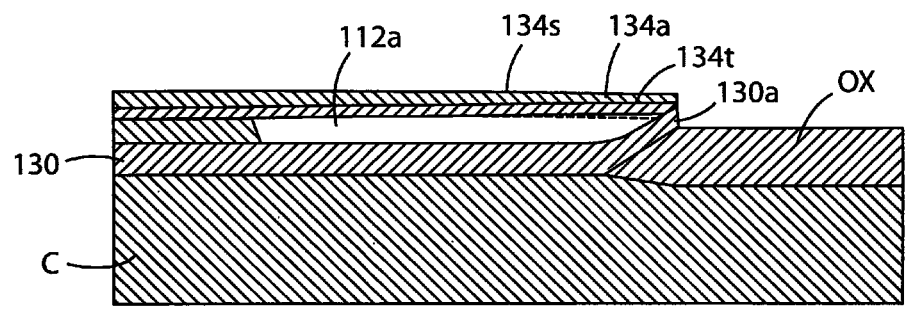
Figure 14C:
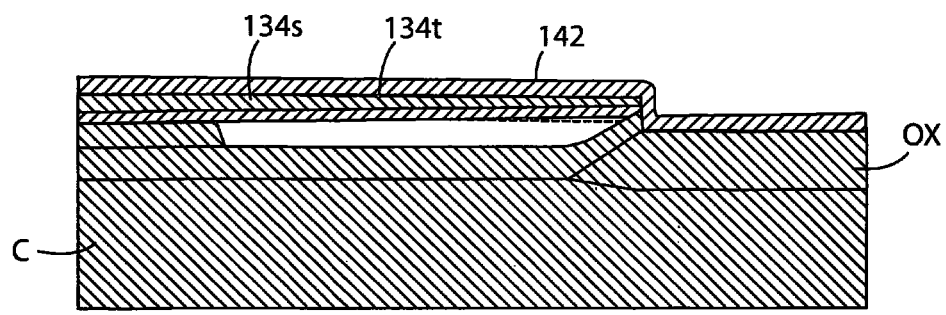

FIGS. 14A, 14B, 14C illustrate still another alternative embodiment for sealing of the longitudinal edge or side of a microchannel regions 112a, 112b defined between the first and third thin films or layers 130, 134 of $Si_3N_4$ by wall 113 formed by partially etching the second thin film or layer 132 of $SiO_2$. This embodiment addresses the case the sealing is performed by depositing the sealing layer by a high conformity process, such as CVD. In this alternative embodiment, the first thin film or layer 130 comprises a low stress SiN layer and the third thin film or layer 134 is modified to comprise a dual layer structure comprising a low stress SiN layer 134s and high stress SiN layer 134t that bends in response to residual internal stress toward the first thin layer or film 130, as shown in FIG. 14A, to reduce the size of the gap at the outermost edges of these films or layers. A low stress SiN film or layer is deposited by LPCVD (low stress nitride process, based on higher Si content in the film and higher deposition temperatures, such as 875 degrees C.), while a high stress SiN is deposited by standard LPCVD stoichiometric nitride deposition process.

Figure 14D:
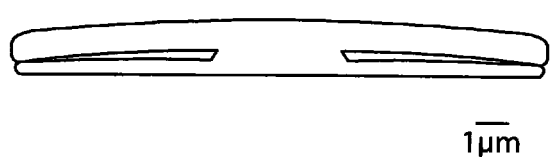
FIG. 14D is a photomicrograph of a transversely sectioned cantilever sealed by a sealing layer that extends partially inside the microchannel.

FIG. 14B shows the effect of selective oxidation of the chip substrate C to cause the first film or layer 130 to bend toward the third film or layer 134 to form an outermost angled region 130a at an outmost edge thereof concurrently with the selective oxidation. A low stress SiN sealing layer 142 then is deposited on the third thin film or layer 134 to seal the smaller gap with reduced penetration of the sealing layer into the microchannel regions 112a, 112b, FIG. 14C. FIG. 14D is a photomicrograph showing the sealing layer deposited partially inside the microchannel regions of an actual microfabricated cantilever that has been transversely sectioned.

Figure 15U:
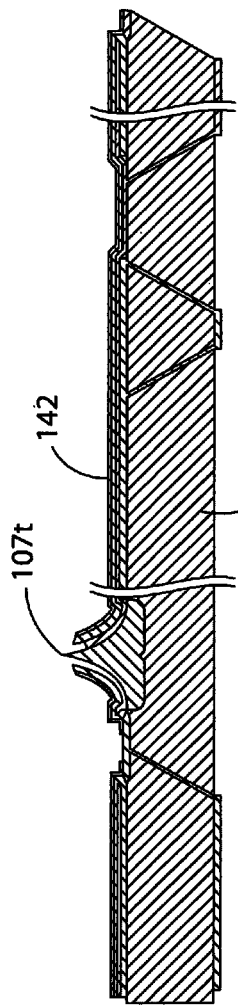
Figure 15V:
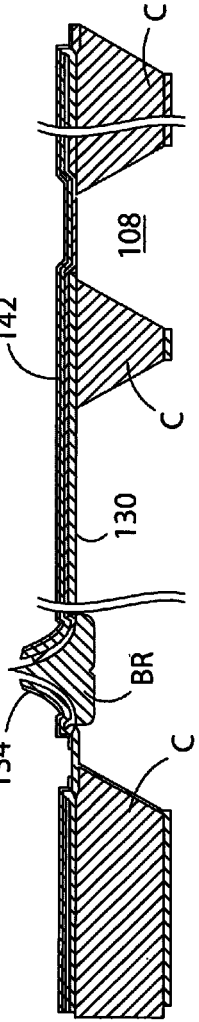
Figure 15X:
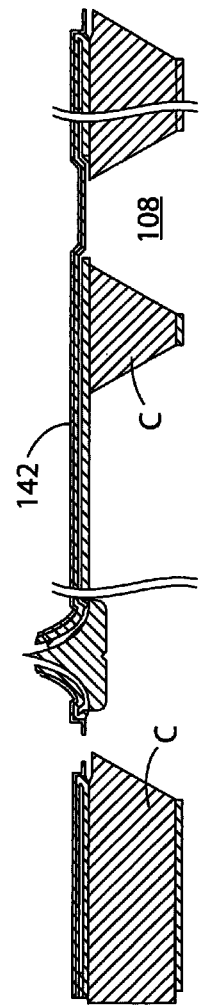
Figure 15Y:
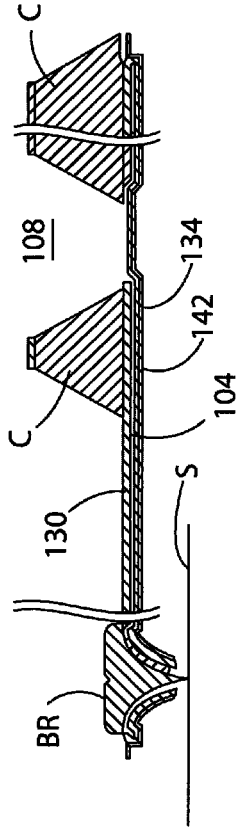

FIGS. 15A through 15Y (where like features of previous figures are designated by like reference numerals) illustrate an embodiment of the invention in which a sharper tip is microfabricated on a cantilever 102 and the connectivity (communication) of the microchannels 104 to the shell-to-core annular space 110 of the dispensing tip is increased, to work with a subsequent high conformity sealing layer deposition, leading to improved sealing of the microchannels.

FIGS. 15A through 15B illustrate a microfabrication method for forming a sharp tip body 107 by depositing a masking layer 200, patterning it by lithographic means and etching the silicon substrate isotropically, followed by oxidation sharpening (this process reproduces the previous process described in FIG. 8A). FIG. 15C illustrates the lithographic removal of the oxide 202 around the tip body 107 by wet etching, such as using buffered hydrofluoric acid and the ion implantation of an etch stop dopant, such as boron $5\times10^{19}$ $B/cm^3$, to form an implanted tip body region BR followed by the removal of the oxide by buffered hydrofluoric acid, FIG. 15D. Then, a first thin film layer 130, such as low stress silicon nitride of thickness from 0.25 µm to 1 µm, and a temporary masking layer 206, such as oxide of thickness from 0.25 µm to 0.5 µm, are deposited by LPCVD methods. A lithographic mask 208 is applied to define an exposed region around the tip body 107 that is 1-4 µm less in radial size than the ion implanted region BR and also defining simultaneously the shape of the future reservoir, FIG. 15E. The temporary masking layer 206, such as oxide, is wet etched using buffered hydrofluoric acid in the openings of the photoresist mask, FIG. 15F. The photoresist is removed, and the first layer 130, such as nitride, is wet etched to expose the pointed tip 107t on the substrate C, such as using hot phosphoric acid in the openings provided by the temporary masking layer 206, FIG. 15G. Then, the temporary masking layer 206, such as oxide, is removed by buffered hydrofluoric acid, FIG. 15H. Then, a second thin film layer 132, such as low temperature silicon oxide, and a third thin film layer 134, such as low stress silicon nitride, are deposited on the substrate by LPCVD, FIG. 15I, and patterned lithographically to define the shape of the cantilever precursor and future channels, FIG. 15J. The third thin film layer 134 can eventually be a sandwich of high stress nitride and low stress nitride, such as in the process described in FIGS. 13A-13D, to provide later a better sealing by bending the third thin film layer 134 towards the first thin film layer 130. The third, second and first thin film layers are etched through the lithographic mask 210, using reactive ion etching, such as with $CF_4$ gas, FIG. 15K. Then, a selective wet chemical etching of the second thin film layer 132 is performed, such as by using buffered hydrofluoric acid, to define concurrently the open-side microchannels 104 and shell-to-tip annular space 110 of the dispensing microtip 106, FIG. 15L. The etching of the second thin film layer 132 at this step is to be performed until the second thin film layer is etched around the apex of the tip body 107. If the desired width of the microchannels 104 is etched before the second thin film layer is etched away around the apex of the tip body 107, an additional lithographic mask 214 can be applied and the second thin film layer etching can be subsequently continued locally, only around the tip body 107, as illustrated in FIG. 15M. After the etching of the second thin film layer 132 is conducted to form the desired size of microchannels 104 and shell-to-core annular space 110 at the dispensing tip, a thermal oxidation of the silicon chip C at area OX for example is performed, FIG. 15N, to provide an angling of the first thin film layer 130 so as to close the gap or space at the outermost edges of the microchannel 104, through a process known as "birds beak oxidation" for those skilled in the field and/or as described above with respect to FIGS. 9A-9C, 13A-13D, and 14A-14D. Subsequently, a sealing layer 142, including but not limited, to a low stress silicon nitride is deposited by any deposition method, including but not limited to LPCVD. In case of a deposition method of high conformity, such as LPCVD, the sealing layer 142 may cover the inner surfaces of the microchannels 104 and the annular space 110 around the tip body 107, without affecting their future fluid communication, FIG. 15P. The device microfabrication continues by defining the future cantilever shape lithographically, FIG. 15Q, via patterning with photoresist 216 of the sealing layer 142, using a selective etching such as like $CF_4$ RIE in case the sealing layer is silicon nitride. The same photoresist layer or another photoresist layer can be used to first decover the tip apex 107t by thinning the photoresist with oxygen plasma etching, then to continue with reactive ion etching (such as $CF_4$ RIE) to etch the sealing layer 142 and the third thin film layer 134 around the tip apex 107t, FIGS. 15S and 15T which also present the schematic evolution of the tip shape during the etching process. After the complete removal of the photoresist by using oxygen plasma or/and commercial photoresist remover, the device structure appears as shown in FIG. 15T. Then, the backside alignment and lithography are performed, eventually using a mask containing convex corner compensation beams, such as the one in FIG. 8L. The backside masking layer corresponds to the first, second, third and sealing thin film layers, which can be removed sequentially using reactive ion etching, such as $CF_4$ RIE, or combinations of RIE and wet chemical etching, FIG. 15U. Then, a backside silicon etching of the silicon chip substrate C is performed using a front-side protecting holder and 40% (mass ratio) KOH solution at 80 degrees C., or any other method of etching of the silicon chip substrate while protecting the structures on the front side of the chip substrate, FIG. 15V. The backside silicon removal step also defines the reservoir 108 and the chip substrate C eventually mechanically attached to a larger silicon frame for easy handling, while leaving the cantilever structure embedded in a composite membrane composed of oxide, the first, second, third and the sealing thin film layers, out of which the oxide and the second thin film layer are subsequently wet-etched, such as using buffered hydrofluoric acid, FIG. 15X. If necessary, the backside of the chip substrate can be further etched using $CF_4$ RIE to connect the microchannels 104 to the reservoir 108 by removing the sealing layer 142 eventually covering the inner side surfaces of the microchannels. A very thin metal layer, such as including but not limited to Au 15 nm, can be deposited on the backside of the chip substrate C in order to increase the reflection of the cantilever 102 for the laser beam eventually used for the control of the AFM probe positioning (optical lever). Use of the fabricated device and microtip to write or probe is achieved with the tip oriented towards the writing or probing surface S as illustrated in FIG. 15Y.

In an embodiment where the device is used as a probe to apply or record electrical signals through the tip 107$t$, the metal used for enhancing the laser reflection properties of the backside of the cantilever 102 can be also used to apply these signals to surface S, since it connects the body of the chip substrate C with the eventually boron doped silicon tip body 107, which is conductive.

FIGS. 16A, 16B and 17, 17A illustrate an embodiment of the invention wherein an actuator 150 is disposed on each cantilever 102 to impart bending motion thereto to move the microtip 106 close enough to the surface S to dispense writing material thereon, or in an embodiment where no material is dispensed, close enough to probe surface S or to apply or record an electrical signal on surface S. The actuator 150 may be selected from any suitable actuator, such as including, but not limited to, a piezoelectric actuator having a piezoelectric film, a thermal actuator having a resistor forming a composite with the rest of the cantilever, with different thermal expansion coefficients, or a magnetic actuator having a magnetic film and others.

Figure 16A:
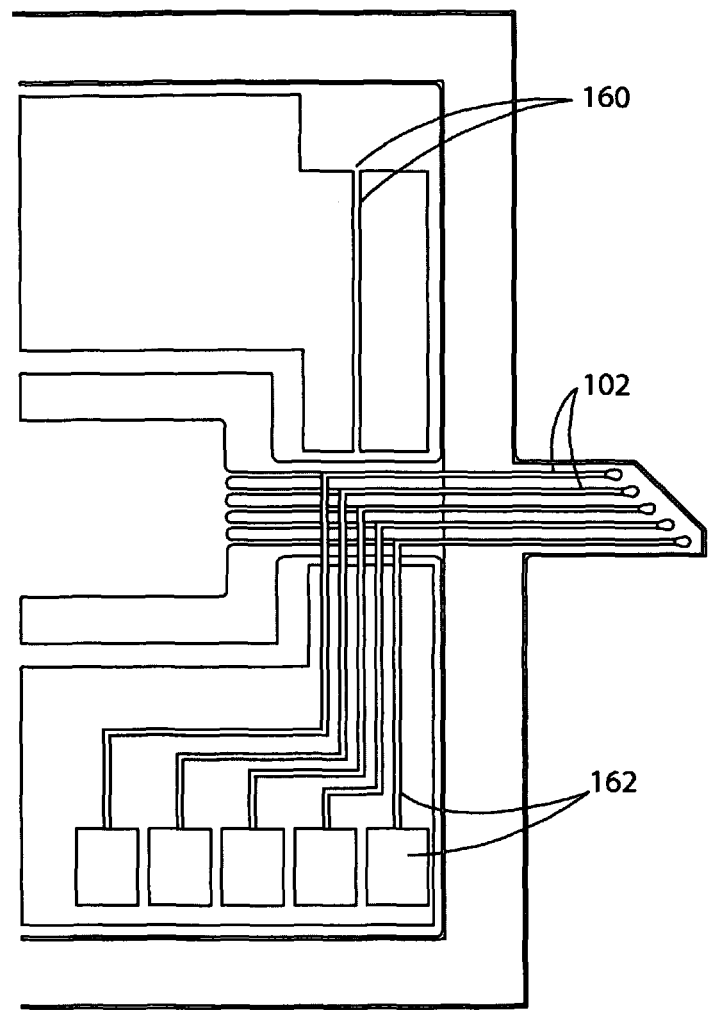
FIG. 16A shows a layout of another illustrative dispensing device for a semiconductor substrate chip wherein piezoelectric actuators are to be formed on the cantilevers during device fabrication.
Figure 16B:
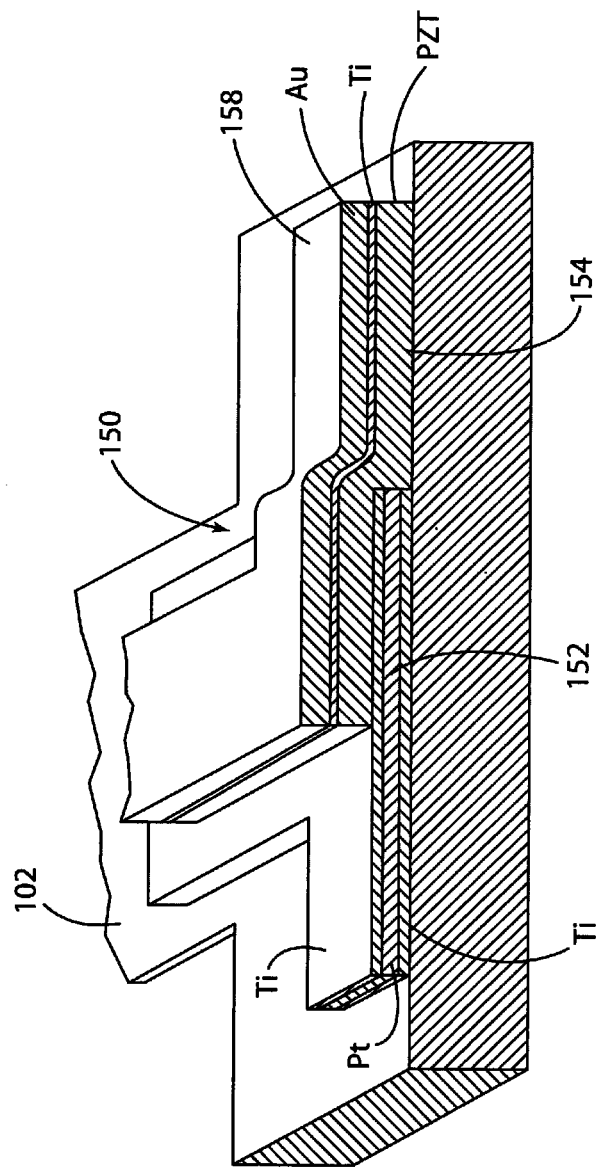
FIG. 16B shows the layout enlarged in the vicinity of the cantilevers showing a piezoelectric film actuator.

Referring to FIGS. 16A, 16B, a piezoelectric actuator 150 is illustrated as being formed on the surface of the cantilever 102 on which the microtip 106 is disposed. The piezoelectric actuator 150 is formed by depositing on that surface a Pt film 152 sandwiched between the Ti films, a piezoelectric (PZT) film 154, and a Au (gold) film 158 separated by a Ti film from the PZT film. The Pt film 152 provides an electrical contact by which the PZT film 154 is connected by electrical lead 160 to ground, and the Au film 158 provides an electrical contact by which the PZT film 154 is connected by electrical lead 162 to a source of electrical voltage or current (not shown) to energize the piezoelectric film 154 in a manner to cause the cantilever 102 to bend toward or away from the surface S. Each actuator 150 thereby can be addressed and actuated independently by a suitable electronic controller, such as a microcomputer (not shown), to independently actuate the cantilevers 102 to move during operation of the dispensing device 100. The first-deposited Pt film can be used eventually also as a reflective layer for enhancing the reflection properties of the cantilever for optical position control within the AFM equipment (optical lever).

Figure 17:
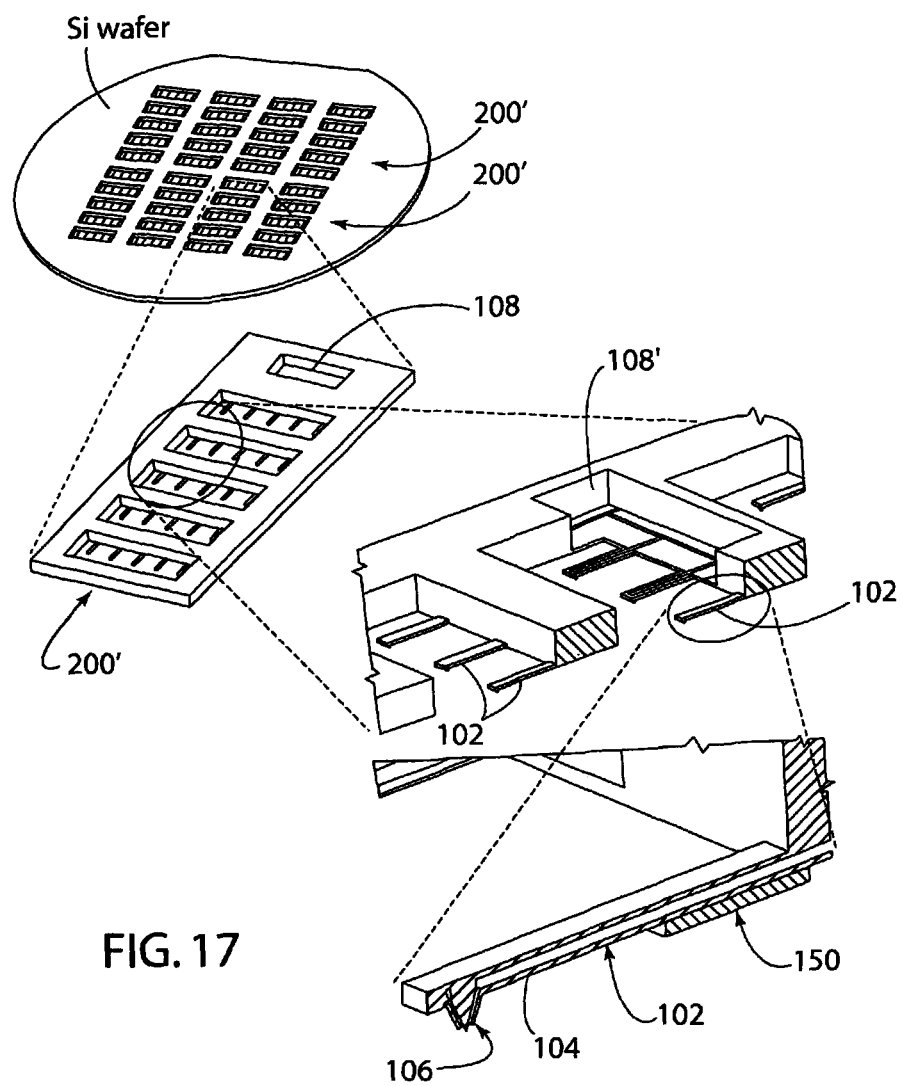
FIG. 17 is an exploded schematic view showing fabrication of a massively parallel array of writing probes using the actuated cantilevers described above pursuant to the invention for high speed direct writing over a large area.

FIG. 17 illustrates schematically fabrication of a dispensing device 200' having a plurality of cantilevers 102 of the type described above integrated in linear and two dimensional arrays as shown for purposes of illustration and not limitation. The device 200' is shown including one common reservoir 108 to supply material to all of the cantilevers 102 but more than one reservoir 108 can be provided as desired. For example, a reservoir 108' could be provided for each row of cantilevers. Each cantilever 102 includes a PZT actuator 150 that is addressed and actuated independently by a suitable controller (not shown). FIGS. 17A shows a cantilever 102 with the actuator 150 thereon. Those skilled in the art will appreciate that one or more other devices 200' can be stacked atop and/or below the device 200' shown to provide stacks of two dimensional cantilevers 102 arrays in a manner to form a three dimensional cantilever array where the cantilevers are independently addressed and actuated by respective integral actuators 150 on the cantilevers 102 in response to a multi-plexed addressing scheme. Such arrays can be used to produce massively parallel active cantilevers for material (e.g. ink, biomolecules, etc.) dispensing applications with continuous-material delivery or feed to material dispensing microtips 106 for high speed direct writing over large surface areas.

For purposes of illustration and not limitation, a dispensing device of the type shown in FIG. 8I was mounted for testing on the tip holder of a conventional atomic force microscope Dimension 3100, Digital Instruments having a closed loop scanner to minimize thermal drift during writing of a pattern on surface. Writing using the dispensing device was tested using 1-octadecanethiol (ODT) and 16-mercaptohexadecanoic acid (MHA) on a Au (gold) surface. After the reservoir 108 was filled with ODT or MHA, the microtip 106 was brought into contact with a solution of ODT or MHA spread on the gold surface for tip-priming purposes. As a writing test, letters with a minimum line width of about 200 nm were successfully obtained by dispensing the ODT or MHA onto the gold surface; then the letters were imaged using the same microtips as for dispensing, in lateral force imaging AFM mode. Imaging in constant force mode was also tested on a calibration standard (Pacific Nanotechnology), consisting of an array of squares, with different lateral sizes in the 1-10 μm range, and heights of 80 nm. The imaging capabilities of the novel microtips of the invention in the tapping and contact modes are completely similar to standard AFM probes (VEECO, NP-20. Likewise, they exceed their resolution and sensitivity in lateral force mode as a result of the lower rotational stiffness in twisting of the cantilevers.

The invention envisions a method of applying an electrical stimulus and measuring the electrical response of a surface in nanometer-scale vicinity of a probing microtip 106 in the presence of a locally created environment at the end of the microtip through which the material is dispensed around the microtip. For example, an electrolyte material, such as including but not limited to, HC1, NaC1, copper sulfate, and the like, can be dispensed from the volcano-shaped microtip 106 of the cantilever 102 onto the surface to create the local environment. The electrical stimulus can be a constant or varying voltage or electrical current applied by the microtip 106 to the surface by appropriate movement of the cantilever 102 to bring the microtip close enough to or in contact with the electrolyte and/or the surface to apply the electrical stimulus thereto or to record an electrical response at a given location on the surface. The method can be used to characterize the dispensed material or the surface at the given location.

The invention is advantageous in providing a material dispensing device that can provide continuous feeding of material to one or more microtips and the possibility to fabricate arrays of material dispensing devices easy to integrate on microfluidic chips and capable of parallel writing with one or several material species.

Although the invention has been described in connection with certain embodiments thereof, those skilled in the art will appreciate that the modifications and changes can be made thereto without departing from the spirit and scope of the invention as set forth in the appended claims.

We claim:

1. A method of dispensing material, comprising supplying material through a microchannel in a cantilever extending from a substrate to a material dispensing tip on the cantilever and dispensing the material from the material dispensing tip on a surface, including imparting a bending motion to the cantilever by energizing a piezoelectric film actuator, a thin film thermal actuator, or a magnetic film actuator disposed on the cantilever.

2. The method of claim 1 including supplying material from a microreservoir on the substrate to the microchannel and then to the dispensing tip.

3. The method of claim 1 wherein the material is dispensed through a hollow dispensing tip.

4. A method of dispensing material, comprising supplying material through a microchannel in a cantilever extending from a substrate to a material dispensing tip on the cantilever and dispensing the material from the material dispensing tip on a surface including using the material dispensing tip to provide an electrical stimulus to at least one of the surface and the dispensed material.

5. The method of claim 4 wherein the electrical stimulus is a constant or varying voltage.

6. The method of claim 4 wherein the electrical stimulus is applied through the dispensing tip placed adjacent to or in contact with at least one of the surface and the dispensed material.

7. A method of dispensing material, comprising supplying material to a plurality dispensing tips residing on respective cantilevers integrated in linear or two dimensional arrays or in stacks of two dimensional arrays to form a three dimensional array, independently addressing a respective actuator on each of the cantilevers, and dispensing the material from a respective dispensing tip on a surface.

8. A method of dispensing material, comprising supplying material through a microchannel in a cantilever extending from a substrate to a material dispensing tip on the cantilever and dispensing the material from the material dispensing tip by at least one of (a) surface diffusion and (b) surface diffusion and capillary action on a surface.

9. A method of dispensing material, comprising supplying material comprising a fluid through a microchannel in a cantilever extending from a substrate to a material dispensing tip on the cantilever and dispensing the material from the material dispensing tip on a surface.

10. The method of claim 9 wherein the fluid is alkanethiol liquid solution.

11. A method of dispensing material, comprising supplying material comprising a solid through a microchannel in a cantilever extending from a substrate to a material dispensing tip on the cantilever and dispensing the material from the material dispensing tip on a surface.

12. A method of dispensing material, comprising supplying material through a microchannel in a cantilever extending from a substrate to a material dispensing tip on the cantilever and dispensing the material from the material dispensing tip on a gold surface.

13. A method of dispensing material, comprising supplying material comprising an electrolyte through a microchannel in a cantilever extending from a substrate to a material dispensing tip on the cantilever and dispensing the material from the material dispensing tip on a surface.

14. The method of claim 13 wherein the electrolyte is selected from the group consisting of HCl, NaCl, and copper sulfate.

15. A method of dispensing material, comprising supplying material through a microchannel in a cantilever extending from a substrate to a material dispensing tip on the cantilever and dispensing the material from the material dispensing tip on a surface, including using the dispensing tip to provide an electrical stimulus to at least one of the surface and the dispensed material and measuring an electrical response of at least one of the surface and dispensed material.

16. The method of claim 15 wherein the electrical stimulus is a constant or varying voltage.

17. The method of claim 15 wherein the electrical stimulus is applied through the dispensing tip placed adjacent to or in contact with at least one of the surface and the dispensed material.

18. A method of dispensing material, comprising supplying material comprising a biomolecule through a microchannel in a cantilever extending from a substrate to a material dispensing tip on the cantilever and dispensing the material from the material dispensing tip on a surface.

19. The method of claim 18 wherein the biomolecule comprises DNA.

20. The method of claim 18 wherein the biomolecule comprises a protein.

* * * * *